US009650633B2

(12) United States Patent
Lee et al.

(10) Patent No.: US 9,650,633 B2
(45) Date of Patent: May 16, 2017

(54) COMPOSITION FOR CONTROLLING STEM CELLS PLURIPOTENCY, CONTAINING LIN28A METHYLATION INHIBITOR, AND METHOD FOR SCREENING FOR LIN28A METHYLATION INHIBITOR

(71) Applicant: KOREA ADVANCED INSTITUTE OF SCIENCE AND TECHNOLOGY, Daejeon (KR)

(72) Inventors: Daeyoup Lee, Daejeon (KR); Seung-Kyoon Kim, Daejeon (KR); Hosuk Lee, Jeonju-si (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 14/778,600

(22) PCT Filed: Nov. 3, 2014

(86) PCT No.: PCT/KR2014/010410
§ 371 (c)(1),
(2) Date: Sep. 20, 2015

(87) PCT Pub. No.: WO2015/126033
PCT Pub. Date: Aug. 27, 2015

(65) Prior Publication Data
US 2016/0053258 A1 Feb. 25, 2016

(30) Foreign Application Priority Data

Feb. 19, 2014 (KR) .................. 10-2014-0019261

(51) Int. Cl.
| | |
|---|---|
| *C12N 15/113* | (2010.01) |
| *C07K 16/00* | (2006.01) |
| *C12N 5/0735* | (2010.01) |
| *C07K 16/18* | (2006.01) |
| *C12N 15/115* | (2010.01) |

(52) U.S. Cl.
CPC ............ *C12N 15/113* (2013.01); *C07K 16/18* (2013.01); *C12N 5/0606* (2013.01); *C12N 15/115* (2013.01); *C12N 15/1137* (2013.01); *C12Y 201/01043* (2013.01); *C07K 2317/76* (2013.01); *C12N 2310/14* (2013.01); *C12N 2310/141* (2013.01); *C12N 2310/16* (2013.01); *C12N 2320/30* (2013.01)

(58) Field of Classification Search
CPC .............................. C12N 15/113; C07K 16/00
USPC ........................ 424/174.1; 514/44 A, 44 R
See application file for complete search history.

(56) References Cited

U.S. PATENT DOCUMENTS

| | | | |
|---|---|---|---|
| 2005/0255487 A1* | 11/2005 | Khvorova | ............ A61K 31/713 435/6.11 |
| 2006/0189557 A1 | 8/2006 | Slack et al. | |
| 2007/0031844 A1* | 2/2007 | Khvorova | ............ A61K 31/713 435/6.11 |

OTHER PUBLICATIONS

Byers, T. (CA Cancer Journal, 1999, 49: 353-361).*
Bartel, D., "MicroRNAs: genomics, biogenesis, mechanism, and function", Cell, Jan. 23, 2004, pp. 281-297, vol. 116.
Bentwich, I., et al., "Identification of hundreds of conserved and nonconserved human microRNAs", Nature genetics, Jun. 19, 2005, pp. 766-770, vol. 37, No. 7.
Berezikov, E., et al., "Phylogenetic Shadowing and Computational Identification of Human microRNA Genes", Cell, Jan. 14, 2005, pp. 21-24, vol. 120.
Cho, J., et al., "LIN28A Is a Suppressor of ER-Associated Translation in Embryonic Stem Cells", Cell, Nov. 9, 2012, pp. 765-777, vol. 151.
Chuikov, S., et al., "Regulation of p53 activity through lysine methylation", Nature, Nov. 18, 2004, pp. 353-360, vol. 432.
Cimadamore, F., et al., "SOX2LIN28/let-7 pathway regulates proliferation and neurogenesis in neural precursors", PNAS, Jul. 24, 2013, p. E3017E3026 (Online Publication).
Couture, J., et al., "Structural basis for the methylation site specificity of SET7/9", Nature Structural & Molecular Biology, Jan. 15, 2006, pp. 140-146, vol. 13, No. 2.
Esquela-Kerscher, A., et al., "Oncomirs—microRNAs with a role in cancer", Nature Reviews Cancer, Apr. 2006, pp. 259-269, vol. 6.
Esteve, P., et al., "Regulation of DNMT1 stability through SET7-mediated lysine methylation in mammalian cells", PNAS, Mar. 31, 2009, pp. 5076-5081, vol. 106, No. 13.

(Continued)

*Primary Examiner* — Yan Xiao
(74) *Attorney, Agent, or Firm* — Hultquist, PLLC; Steven J. Hultquist

(57) ABSTRACT

Provided is a composition for controlling pluripotency of stem cells including an LIN28A methylation inhibitor and a screening method of the LIN28A methylation inhibitor, and more particularly, a composition for controlling pluripotency of stem cells including an inhibitor controlling methylation of $135^{th}$ lysine of LIN28A that is methylated by SET7/9, or a composition for treating cancer, and a screening method of the inhibitor, wherein the screening method includes (a) contacting a candidate material with a cell, the cell having a gene introduced thereinto; (b) measuring a methylation level of the $135^{th}$ lysine of the LIN28A; and (c) selecting an inhibitor controlling methylation of the $135^{th}$ lysine of the LIN28A. That is, the present invention relates to a composition for controlling pluripotency of embryonic stem cells, or an anti-cancer composition, and a screening method of the inhibitor. The method of the present invention is possible to screen materials capable of controlling pluripotency of embryonic stem cells or materials having anti-cancer activity, and the materials screened by the method of the present invention may control pluripotency of embryonic stem cells and inhibit growth of cancer cells, which is effective for disorders of stem cell differentiation or preparation of cancer therapeutic agents.

1 Claim, 18 Drawing Sheets

(56) References Cited

OTHER PUBLICATIONS

Friedman, R., et al., "Most mammalian mRNAs are conserved targets of microRNAs", Genome Research, Oct. 27, 2008, pp. 92-105, vol. 19.

Hafner, M., et al., "Identification of mRNAs bound and regulated by human LIN28 proteins and molecular requirements for RNA recognition", RNA, Mar. 12, 2013, pp. 613-626, vol. 19, No. 5.

He, L., et al., "MicroRNAs: Small RNAs With a Big Role in Gene Regulation", Nature Reviews Genetics, Jul. 2004, pp. 522-532, vol. 5.

Heo, I., et al., "Lin28 Mediates the Terminal Uridylation of let-7 Precursor MicroRNA", Molecular Cell, Oct. 24, 2008, pp. 276-284, vol. 32.

Heo, J., et al., "Vernalization-Mediated Epigenetic Silencing by a Long Intronic Noncoding RNA", Science, Jan. 7, 2011, pp. 76-80, vol. 331.

Kim, S., et al., "Human Histone H3K79 Methyltransferase DOT1L Methyltransferase Binds Actively Transcribing RNA Polymerase II to Regulate Gene Expression", The Journal of Biological Chemistry, Sep. 12, 2012, pp. 39698-39709 (Online Publication), vol. 287.

Kim, S., et al., "SET7/9 Methylation of the Pluripotency Factor LIN28A Is a Nucleolar Localization Mechanism that Blocks let-7 Biogenesis in Human ESCs", Cell Stem Cell, Dec. 4, 2014, pp. 735-749, vol. 15.

Kontaki, H., et al., "Lysine Methylation Regulates E2F1-Induced Cell Death", Molecular Cell, Jul. 9, 2010, pp. 152-160, vol. 39.

Kouskouti, A., et al., "Gene-Specific Modulation of TAF10 Function by SET9-Mediated Methylation", Molecular Cell, Apr. 23, 2014, pp. 175-182, vol. 14.

Lewis, B., et al., "Conserved Seed Pairing, Often Flanked by Adenosines, Indicates that Thousands of Human Genes are MicroRNA Targets", Cell, Jan. 14, 2015, pp. 15-20, vol. 120.

Lu, J., et al., "MicroRNA expression profiles classify human cancers", Nature, Jun. 9, 2005, pp. 834-838, vol. 435.

Lytle, J., et al., "Target mRNAs are repressed as efficiently by microRNA-binding sites in the 5' UTR as in the 3' UTR", PNAS, Jun. 5, 2007, pp. 9667-9672, vol. 104, No. 23.

Nishioka, K., et al., "Set9, a novel histone H3 methyltransferase that facilitates transcription by precluding histone tail modifications required for heterochromatin formation", Genes & Development, Feb. 15, 2002, pp. 479-489, vol. 16.

Oh, S., et al., "A lysine-rich region in Dot1p is crucial for direct interaction with H2B ubiquitylation and high level methylation of H3K79", Biochemical and Biophysical Research Communications, Aug. 3, 2010, pp. 512-517, vol. 399.

Piskounova, E., et al., "Oncogenic Lin28A and Lin28B inhibit let-7 microRNA biogenesis by distinct mechanisms", Cell, Nov. 23, 2011, pp. 1066-1079, vol. 147, No. 5.

Qiu, C., et al., "Lin28-mediated post-transcriptional regulation of Oct4 expression in human embryonic stem cells", Nucleic Acids Research, Dec. 4, 2009, pp. 1240-1248, vol. 38, No. 4.

Semrad, K., "Proteins with RNA Chaperone Activity: AWorld of Diverse Proteins with a Common TaskImpediment of RNA Misfolding", Biochemistry Research International, Nov. 2010, Page(s) Article ID 532908, 11 pages, vol. 2011.

Shyh-Chang, N., et al., "Lin28: Primal Regulator of Growth and Metabolism in Stem Cells", Cell Stem Cell, Apr. 4, 2013, pp. 395-406, vol. 12, No. 4.

Subramanian, K., et al., "Regulation of Estrogen Receptor Alpha by the SET7 lysine methyltransferase", Mol Cell, May 9, 2008, pp. 336-347, vol. 30, No. 3.

Thomson, J., et al., "Extensive post-transcriptional regulation of microRNAs and its implications for cancer", Genes & Development, Aug. 1, 2006, pp. 2202-2207, vol. 20.

Viswanathan, S., et al., "Selective blockade of microRNA processing by Lin-28", Science, Apr. 4, 2008, pp. 97-100, vol. 320, No. 5872.

Wang, J., et al., "A protein interaction network for pluripotency of embryonic stem cells", Nature, Nov. 16, 2006, pp. 364-368, vol. 444.

Wilbert, M., et al., "LIN28 binds messenger RNAs at GGAGA motifs and regulates splicing factor abundance", Mol Cell, Oct. 26, 2012, pp. 195-206, vol. 48, No. 2.

* cited by examiner

FIG. 1
1A
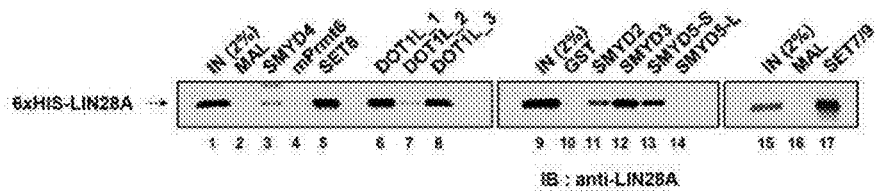
1B
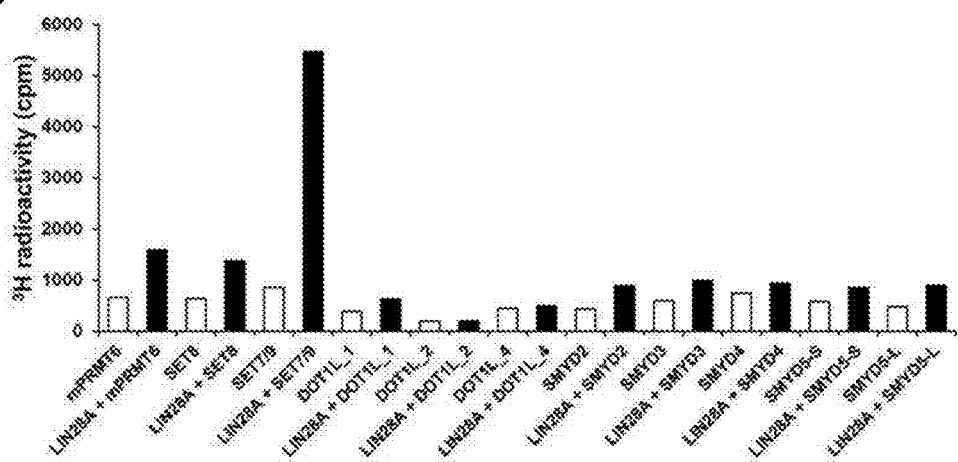

FIG. 3
3A
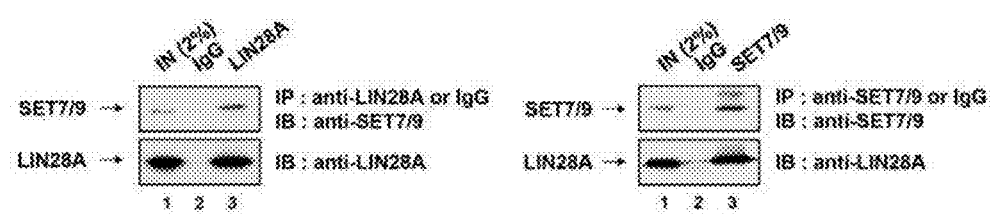
3B
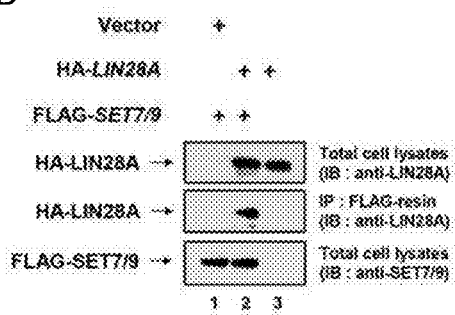
3C
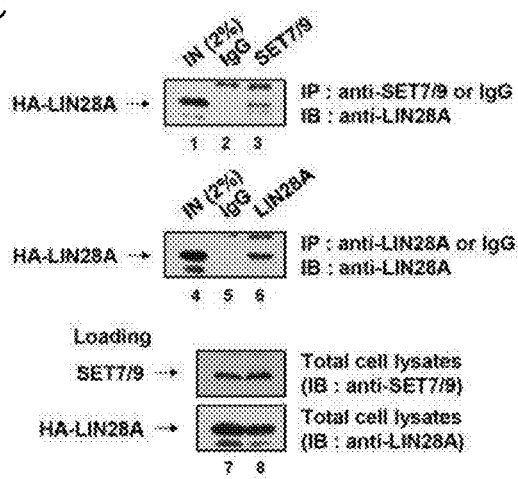
3D
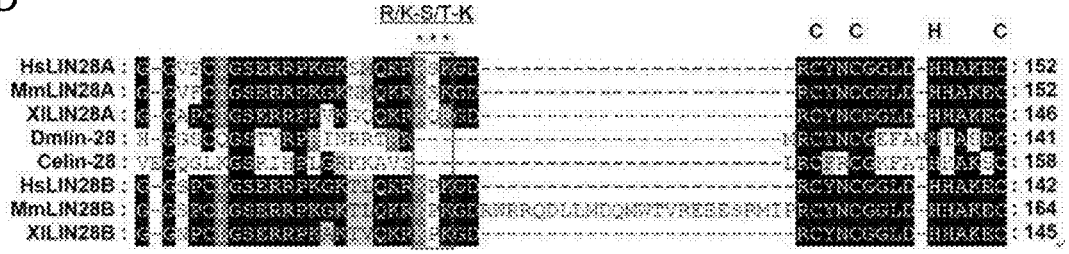

FIG. 4
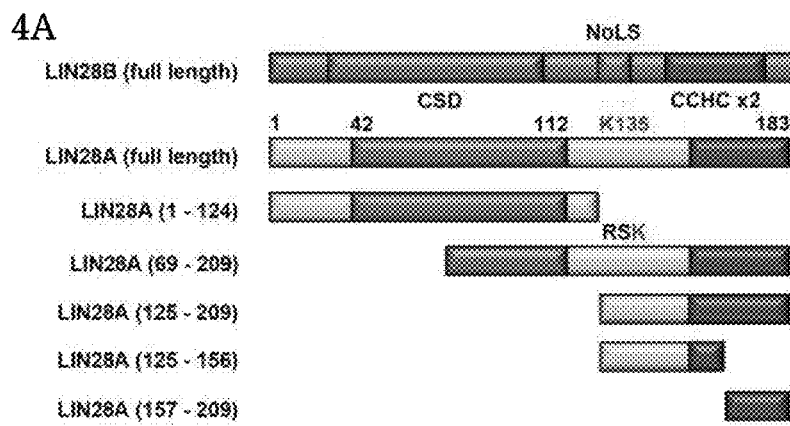
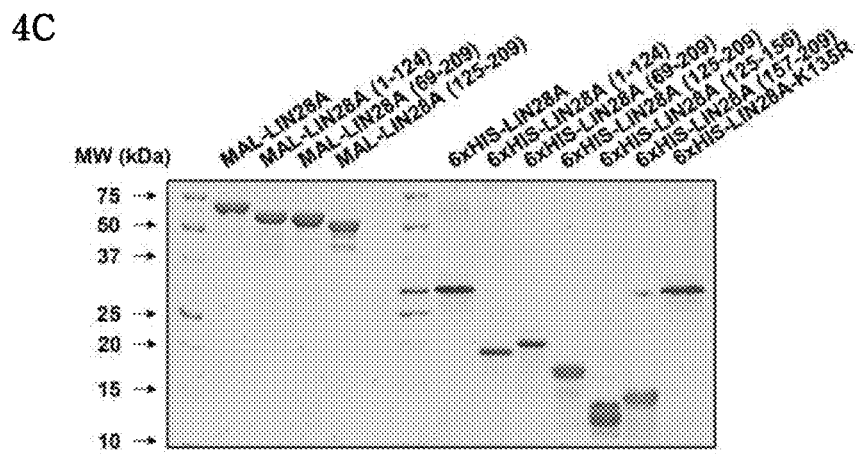
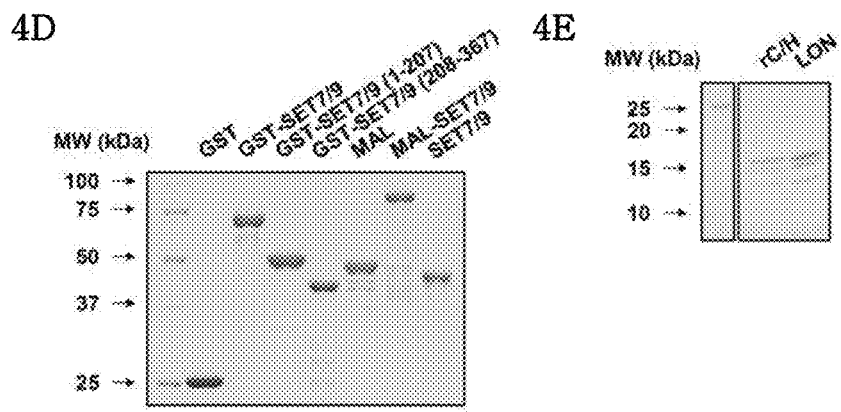

FIG. 5

FIG. 6
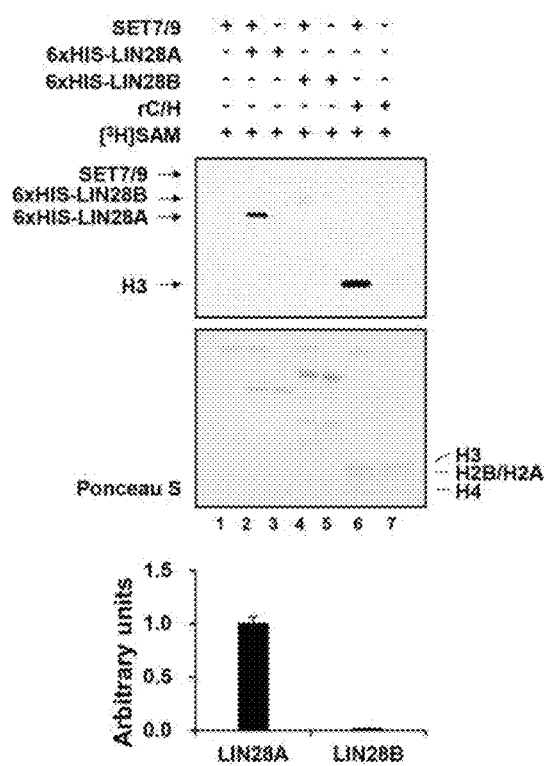 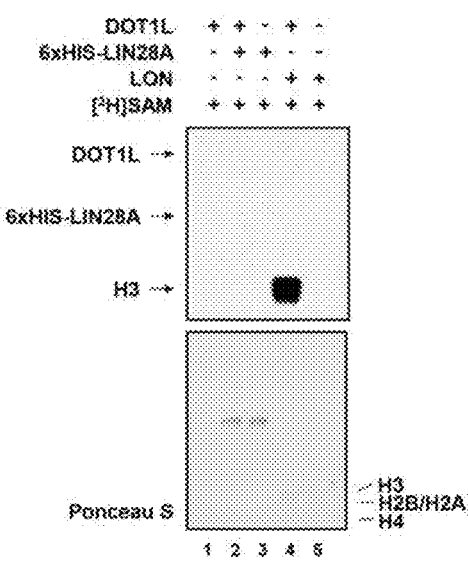

FIG. 8
8A 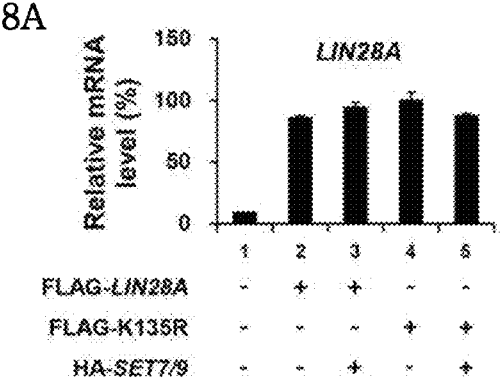
8B 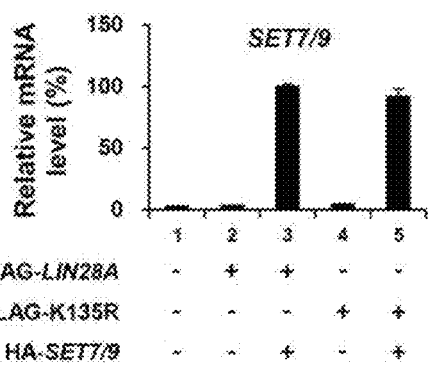
8C 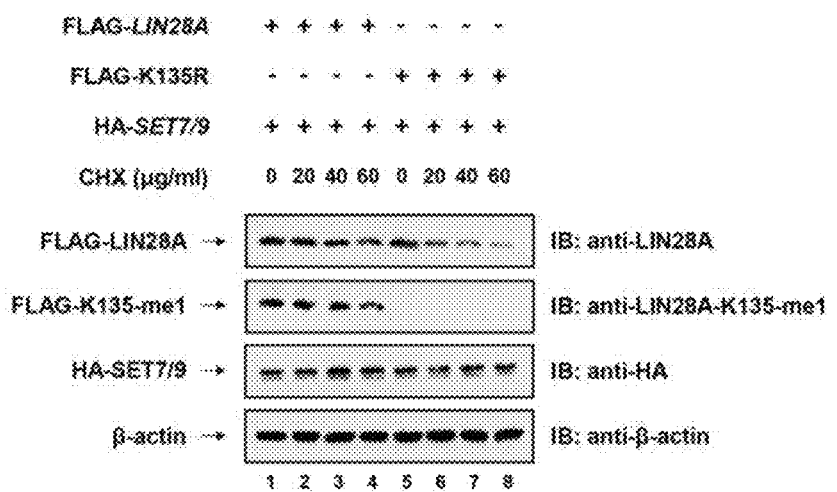
8D 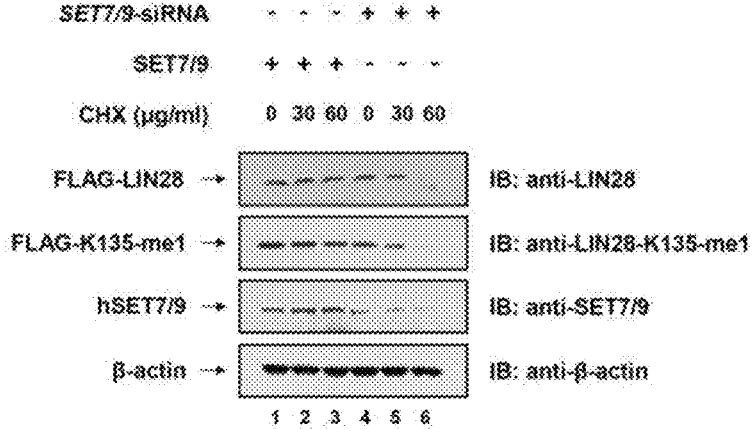

FIG. 9
9A
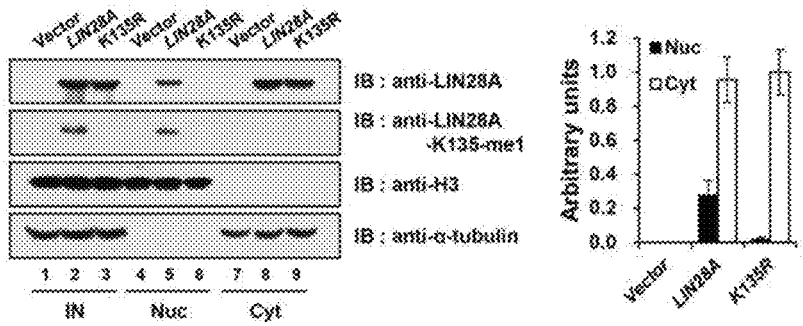
9B 9C
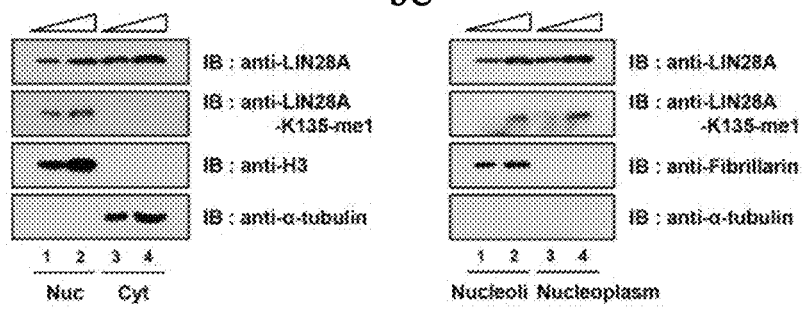
9D
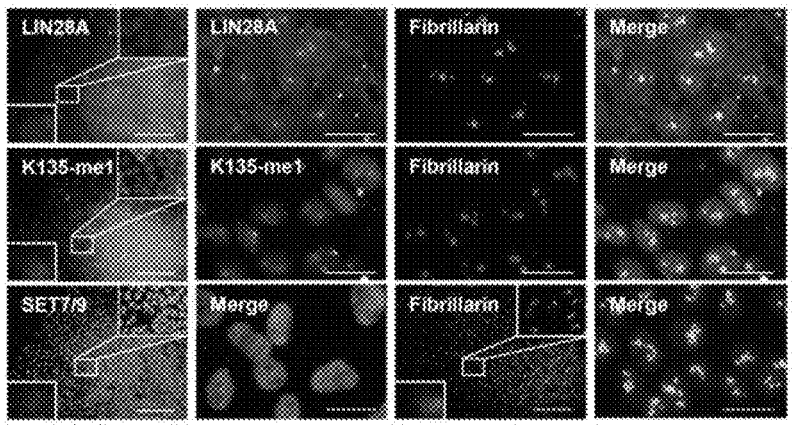
9E
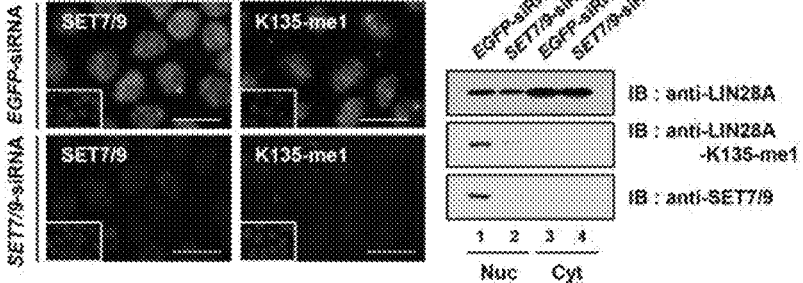

FIG. 10
10A
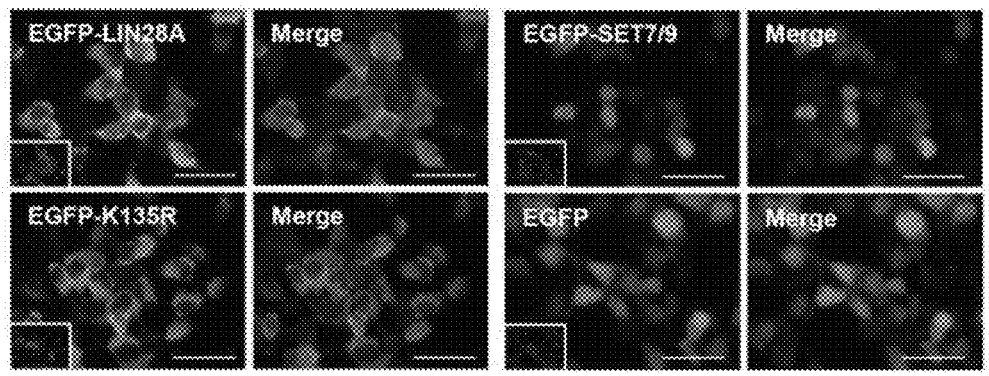
10B
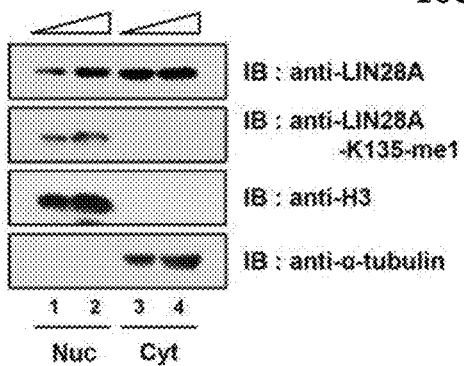
10C
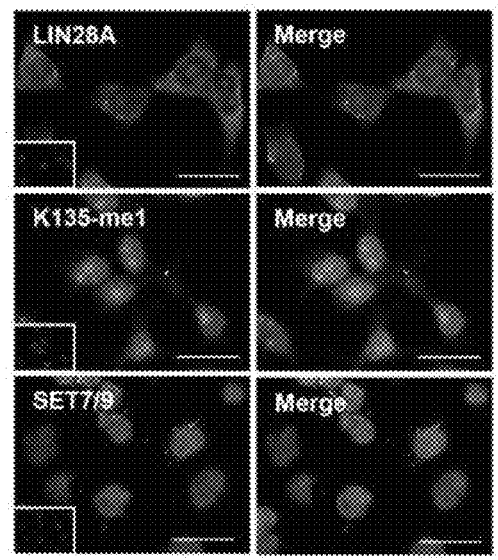
10D

FIG. 11
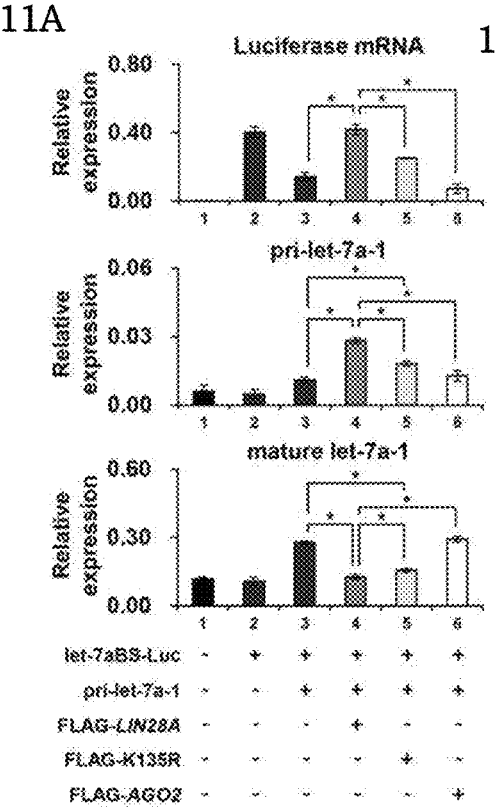
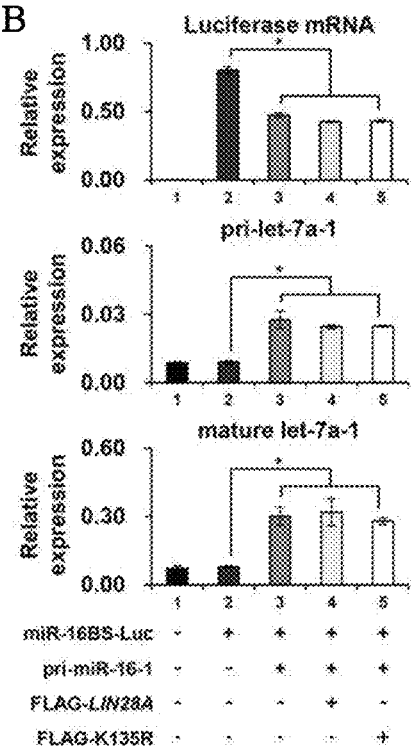
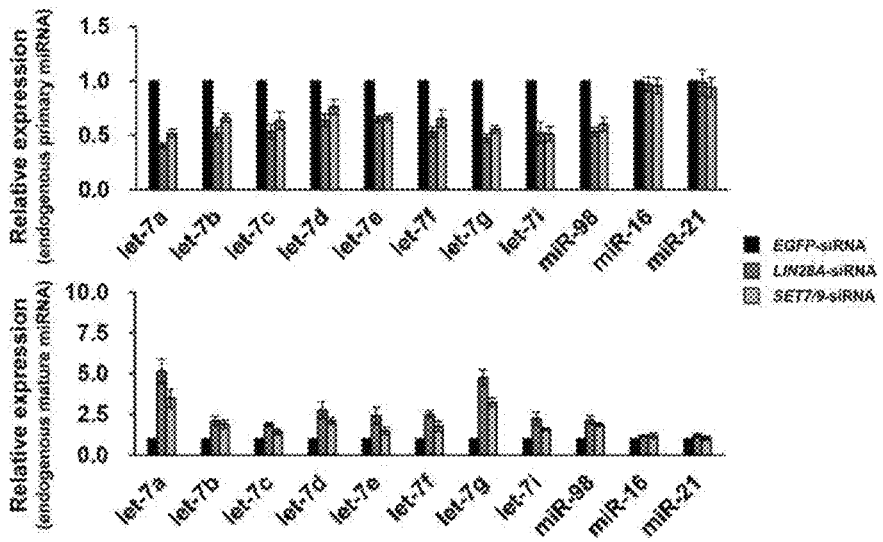

FIG. 12
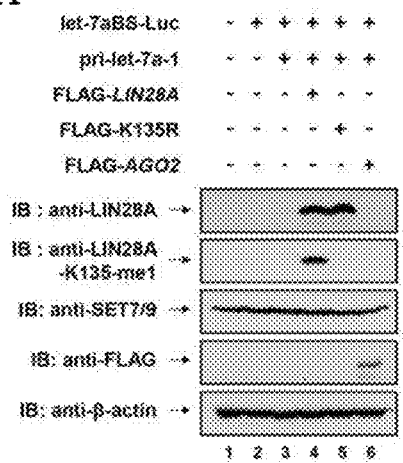
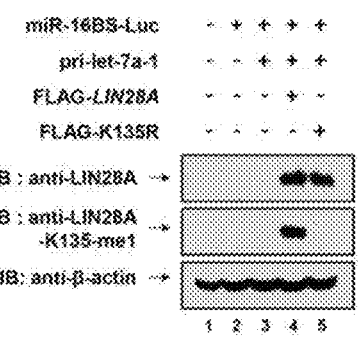
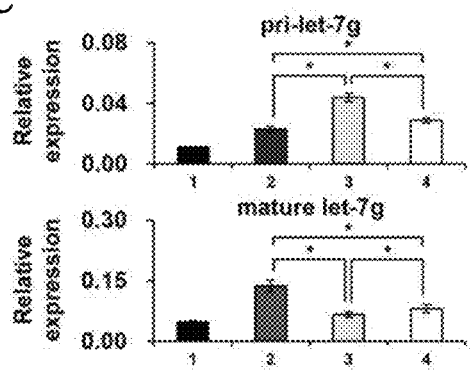
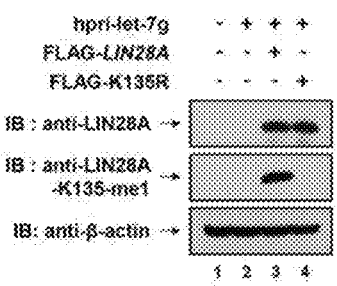
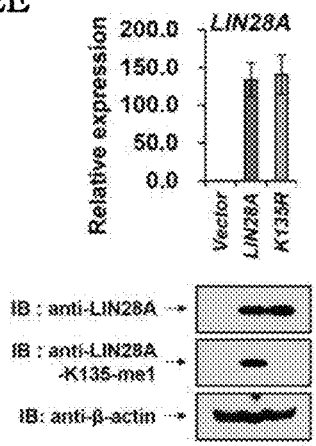
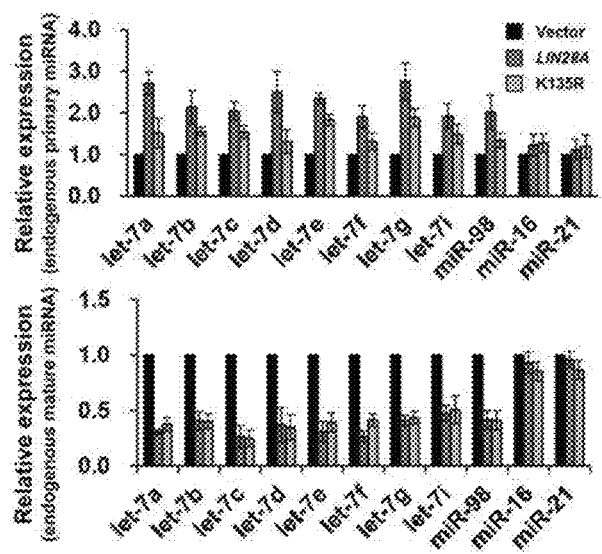

FIG. 13
13A
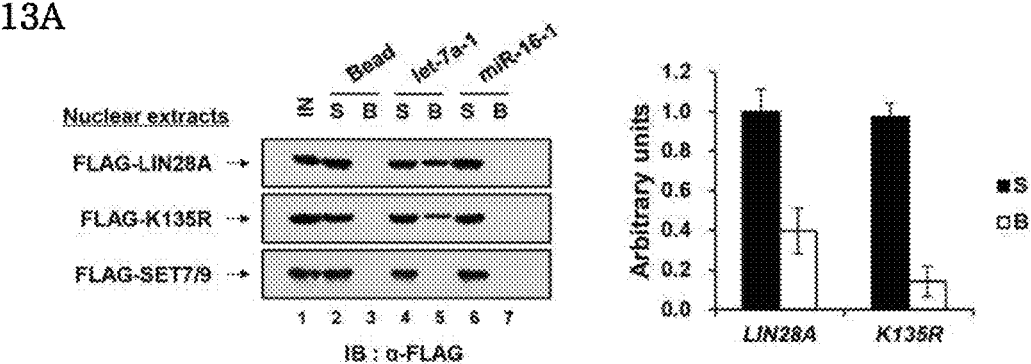
13B
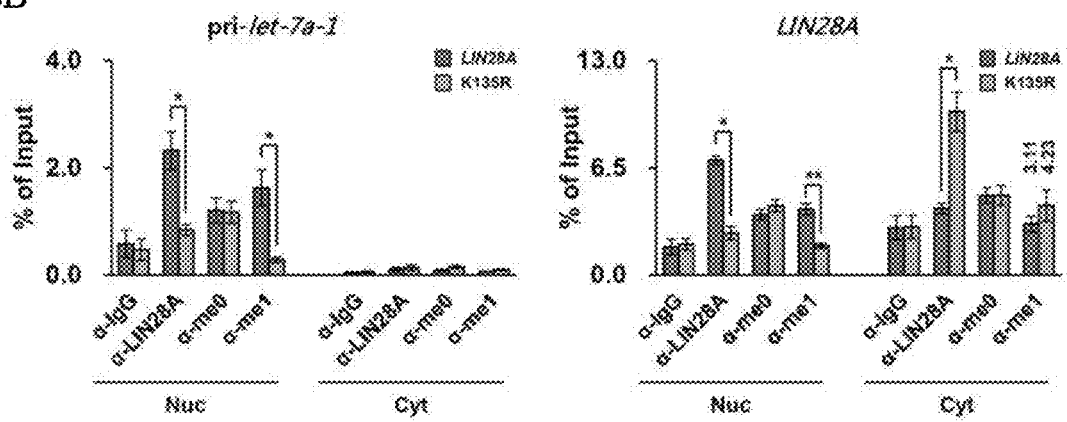

FIG. 14
14A
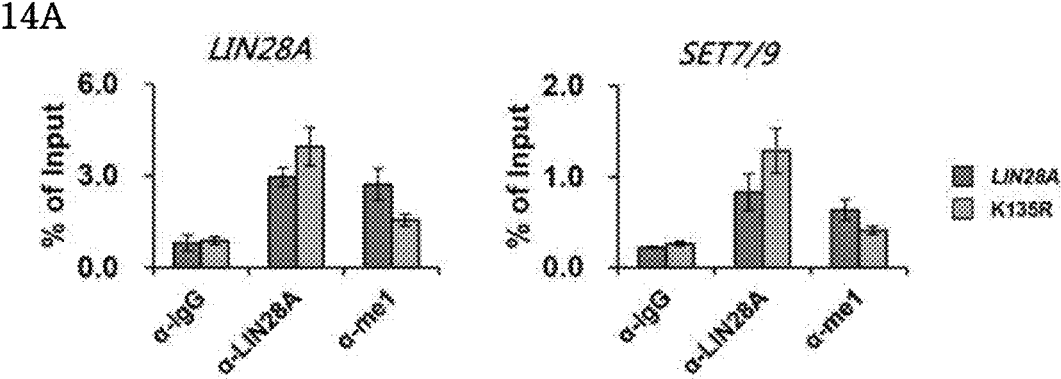
14B
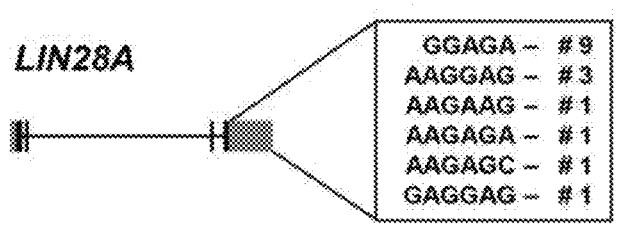
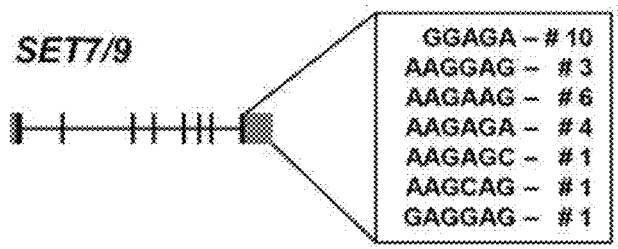
14C
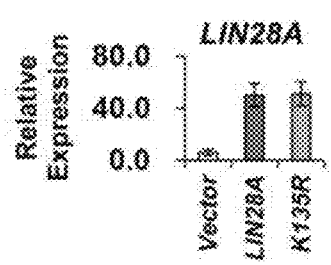
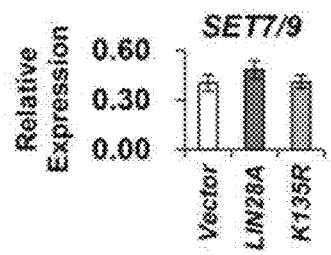
14D
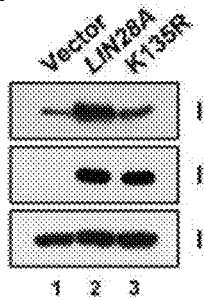
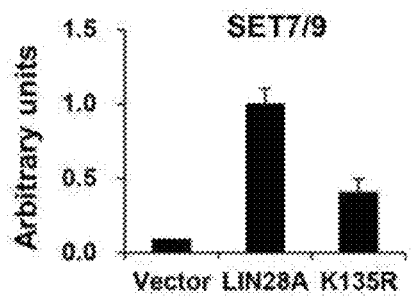

FIG. 16
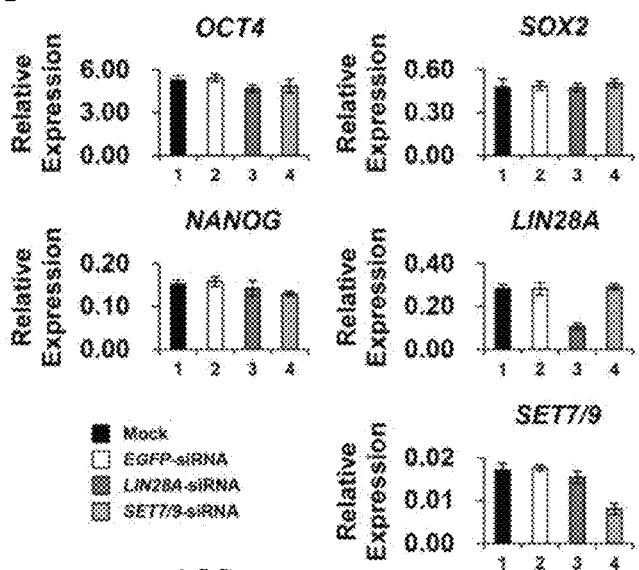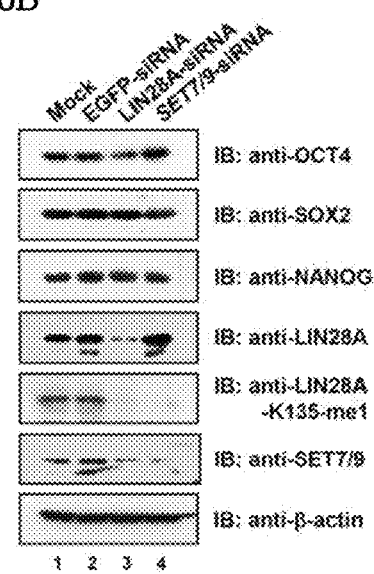
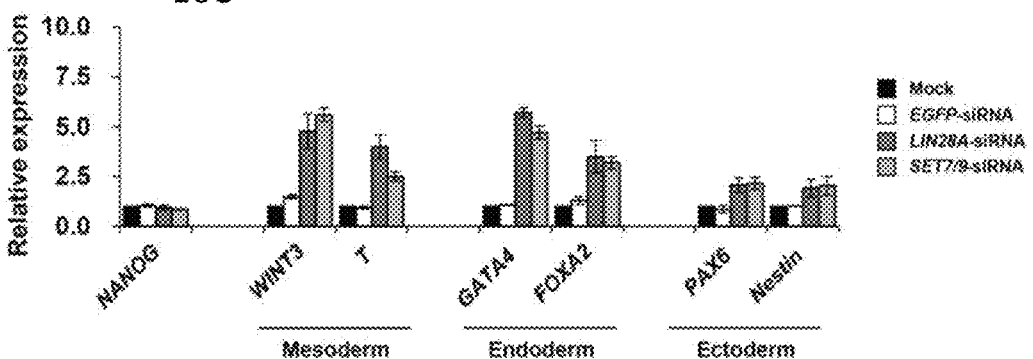

FIG. 17
17A 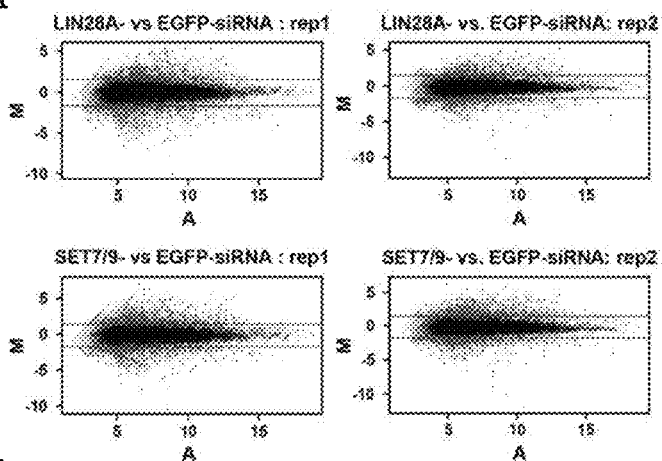
17B 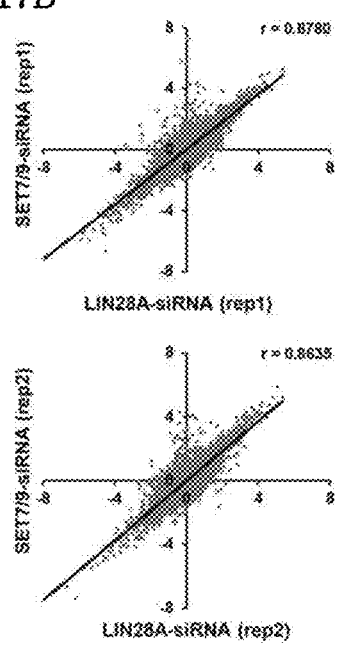
17C 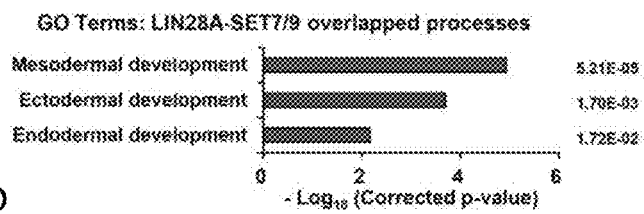
17D 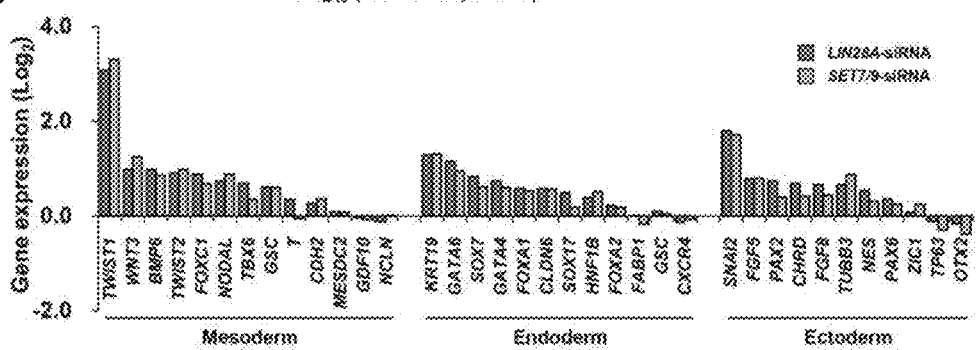

FIG. 18
18A
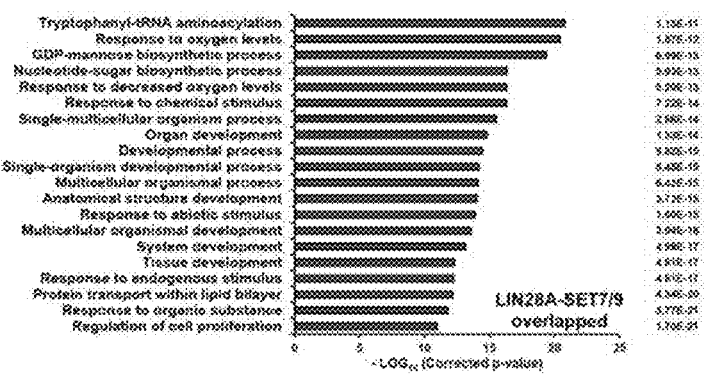
18B
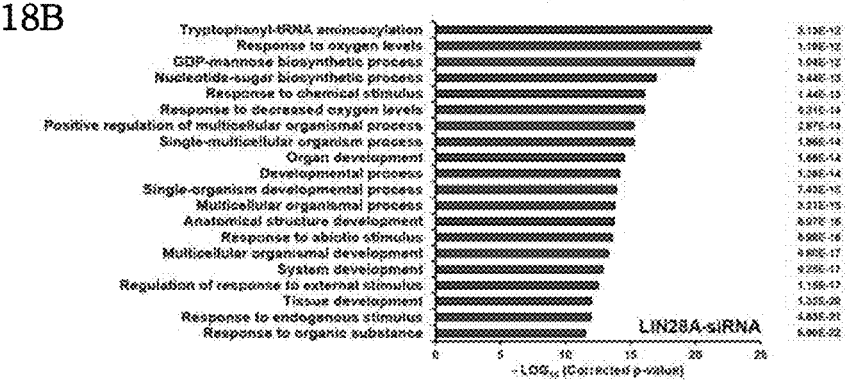
18C
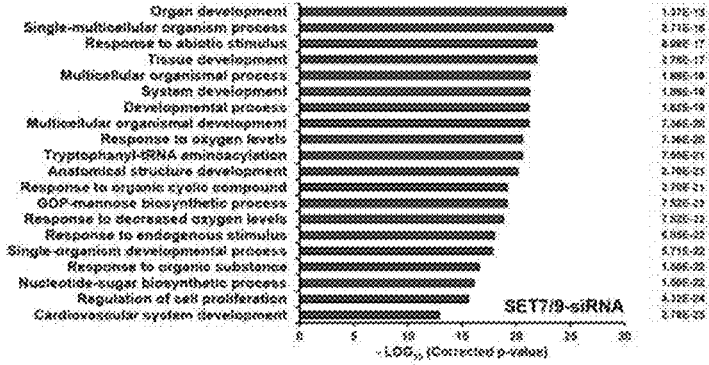
18D
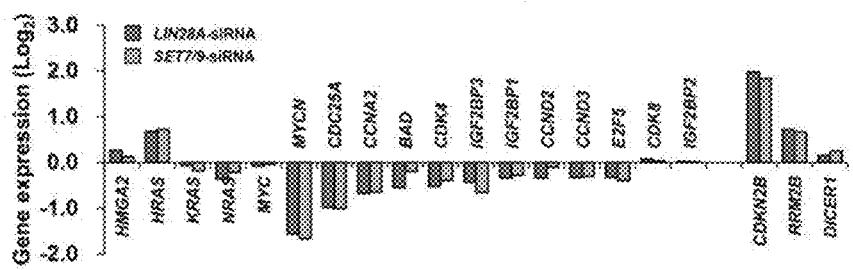

COMPOSITION FOR CONTROLLING STEM CELLS PLURIPOTENCY, CONTAINING LIN28A METHYLATION INHIBITOR, AND METHOD FOR SCREENING FOR LIN28A METHYLATION INHIBITOR

CROSS-REFERENCE TO RELATED APPLICATIONS

This application is a U.S. national phase under the provisions of 35 U.S.C. §371 of International Patent Application No. PCT/KR14/10410 filed Nov. 3, 2014, which in turn claims priority of Korean Patent Application No. 10-2014-0019261 filed Feb. 19, 2014. The disclosures of such international patent application and Korean priority patent application are hereby incorporated herein by reference in their respective entireties, for all purposes.

TECHNICAL FIELD

The present invention relates to a composition for controlling pluripotency of stem cells including a LIN28A methylation inhibitor and a screening method of the LIN28A methylation inhibitor, and more particularly, to a composition for controlling pluripotency of stem cells including an inhibitor controlling methylation of $135^{th}$ lysine of LIN28A that is methylated by SET7/9, or a composition for treating cancer, and a screening method of the inhibitor, wherein the screening method includes (a) contacting a candidate material with a cell, the cell having a LIN28A gene introduced thereinto; (b) measuring a methylation level of the $135^{th}$ lysine of the LIN28A; and (c) selecting an inhibitor controlling methylation of the $135^{th}$ lysine of the LIN28A. That is, the present invention relates to a composition for controlling pluripotency of embryonic stem cells, or an anti-cancer composition, and a screening method of the inhibitor.

BACKGROUND ART

A stem cell is a cell capable of being differentiated into various cells configuring biological tissues, and includes all of undifferentiated cells in steps before being differentiated, obtainable from each tissue of embryos, fetuses and adults. Among various stem cells, a pluripotent stem cell refers to a stem cell having poly-functionality which is capable of being differentiated into all of three germ layers configuring a living body.

The stem cell may be divided into an embryonic stem cell (ES cell) that is separated from embryo, and an adult stem cell that is separated from an adult, depending on separated objects. In addition, the stem cell may be divided into a pluripotent stem cell, a multipotent stem cell, and a unipotent stem cell according to the number of differentiated cells created from one stem cell. In general, an embryonic stem cell (ES cell) may be included in the pluripotent stem cell, an adult stem cell may be included in the multipotent stem cell and the unipotent stem cell.

It is known that micro RNA (miRNA) is a short single-stranded ribonucleic acid (RNA) having 19 to 25 nucleotides in length, and is expressed in cells to control expression of a number of genes (Bartel D. P., (2004) Cell, 116(2):281-97; He L. and Hannon G. J., (2004) Nat. Rev. Genet., 5(7):522-31). Until now, approximately 700 species of miRNAs are found in a human. Since one miRNA is possible to control various kinds of mRNAs, it is predicted that about 30% of human genes are regulated by miRNA (see Bentwich, et al., Nat. Rev. Genet., 37(7):766-70, 2005; Berezikov, et al., Cell, 120(1):21-4, 2005; Lewis, et al., Cell, 120(1):15-20, 2005; Krek, et al., Nat. Genet., 37:495-500, 2005; Friedman, et al., Genome Res., 19:92-105, 2009). let-7 miRNA is one of miRNA, and related to generation of embryo, occurrence of cancer cell, and the like. When the let-7 miRNA is not normally created or does not properly function, problem may occur in an embryonic development process, and cancer may be developed. U.S. Patent Laid-Open Publication No. 2006/0189557 discloses a method for treating cancer by introducing let-7 miRNA into a cancer cell to inhibit activity of RAS oncogene.

LIN28A is a conserved RNA-binding protein, and an expression thereof is strictly regulated in an animal developmental process. LIN28A plays an important role in the generation and particular diseases. For example, LIN28A is highly expressed in embryonic stem cells, and is one of four factors required for changing fibroblasts in humans or mice to induced pluripotent stem cells (iPSCs). A mechanism in which LIN28A is activated in the nucleus has not been found so far.

DISCLOSURE

Technical Problem

The present inventors studied a material capable of controlling pluripotency of stem cells, found that methylation of $135^{th}$ lysine of LIN28A protein of a human embryonic stem cell is related with pluripotency of stem cells, and LIN28A is bound to SET7/9 to induce methylation of $135^{th}$ lysine affects control of pluripotency by controlling the let-7 miRNAs, and completed the present invention.

Therefore, an object of the present invention is to provide a composition for controlling pluripotency of embryonic stem cells, including an inhibitor controlling methylation of $135^{th}$ lysine of LIN28A that is methylated by SET7/9.

Another object of the present invention is to provide a composition for treating cancer, including an inhibitor controlling methylation of $135^{th}$ lysine of LIN28A that is methylated by SET7/9.

Another object of the present invention is to provide a screening method of a material for inhibiting pluripotency of embryonic stem cells, the screening method including: contacting a candidate material with a cell, the cell having a LIN28A gene introduced thereinto; measuring a methylation level of $135^{th}$ lysine of the LIN28A; and selecting an inhibitor controlling methylation of the $135^{th}$ lysine of the LIN28A.

Another object of the present invention is to provide a screening method of a material for inhibiting pluripotency of embryonic stem cells, the screening method including: contacting a candidate material with a cell, the cell having a LIN28A gene introduced thereinto; measuring a binding level of LIN28A and SET7/9; and selecting an inhibitor controlling the binding level of LIN28A and SET7/9.

Another object of the present invention is to provide a screening method of an anti-cancer material, the screening method including: contacting a candidate material with a cell, the cell having a LIN28A gene introduced thereinto; measuring a methylation level of $135^{th}$ lysine of the LIN28A; and selecting an inhibitor controlling methylation of the $135^{th}$ lysine of the LIN28A.

Another object of the present invention is to provide a screening method of an anti-cancer material, the screening method including: contacting a candidate material with a cell, the cell having a LIN28A gene introduced thereinto;

measuring a binding level of LIN28A and SET7/9; and selecting an inhibitor controlling the binding level of LIN28A and SET7/9.

Technical Solution

In order to achieve the above-described objects of the present invention, the present invention provides a composition for controlling pluripotency of embryonic stem cells, including an inhibitor controlling methylation of 135$^{th}$ lysine of LIN28A that is methylated by SET7/9.

In order to achieve another object of the present invention, the present invention provides a composition for treating cancer, including an inhibitor controlling methylation of 135$^{th}$ lysine of LIN28A that is methylated by SET7/9.

In order to achieve another object of the present invention, the present invention provides a screening method of a material for inhibiting pluripotency of embryonic stem cells, the screening method including: contacting a candidate material with a cell, the cell having a LIN28A gene introduced thereinto; measuring a methylation level of 135$^{th}$ lysine of LIN28A; and selecting an inhibitor controlling methylation of the 135$^{th}$ lysine of LIN28A.

In order to achieve another object of the present invention, the present invention provides a screening method of a material for inhibiting pluripotency of embryonic stem cells, the screening method including: contacting a candidate material with a cell, the cell having a LIN28A gene introduced thereinto; measuring a binding level of LIN28A and SET7/9; and selecting an inhibitor controlling the binding level of LIN28A and SET7/9.

In order to achieve another object of the present invention, the present invention provides a screening method of an anti-cancer material, the screening method including: contacting a candidate material with a cell, the cell having a LIN28A gene introduced thereinto; measuring a methylation level of 135$^{th}$ lysine of LIN28A; and selecting an inhibitor controlling methylation of the 135$^{th}$ lysine of LIN28A.

In order to achieve another object of the present invention, the present invention provides a screening method of an anti-cancer material, the screening method including: contacting a candidate material with a cell, the cell having a LIN28A gene introduced thereinto; measuring a binding level of LIN28A and SET7/9; and selecting an inhibitor controlling the binding level of LIN28A and SET7/9.

DESCRIPTION OF DRAWINGS

FIG. 1 shows results of in vitro pull-down assay of various histone methyltransferases and LIN28A.

FIG. 1A shows results of in vitro pull-down assay for confirming interaction of various histone methyltransferases and LIN28A. The pull-down assay was performed at 4° C., and a washing process was performed four times with a binding buffer. The combined sample was analyzed by SDS-PAGE, and an immunoblot analysis was performed with antibodies shown in FIG. 1A.

FIG. 1B shows results of in vitro methyltransferases assay. Various histone methyltransferases of MAL-mPRMT6, MAL-SET8, MAL-SET7/9, MAL-DOT1L (1-467), (468-1002), (1-1002), GST-SMYD2, GST-SMYD3, MAL-SMYD4, GST-SMYD5-S, and GST-SMYD5-L were purified in a bacterial expression system, and reacted with full-length 6×HIS-LIN28A and [$^3$H] SAM.

FIG. 2A shows immunoprecipitation results of endogenous LIN28A expressed in a H9 cell line and SET7/9.

FIG. 2B shows immunoprecipitation results of SET7/9 and LIN28A expressed in a HEK293T cell line.

FIG. 2C shows sequence comparison results of LIN28A and SET7/9 and other proteins targeting lysine methylation.

FIG. 2D shows experimental results showing specificity of antibodies specifically bound to K135-methylated protein of LIN28A. This shows dot blot results of anti-LIN28A-K135-me0 antibody or anti-LIN28A-K135-me1 antibody with respect to LIN28A-K135-me0 (a peptide unmethylated at K135) and LIN28A-K135-me1 (a peptide methylated at K135), and a loading control was confirmed by Ponceau S staining.

FIG. 2E shows results obtained by detecting mono-methylated LIN28A by performing immunoblot on lysates of HEK293T cells in which FLAG-labeled LIN28A wild-type or FLAG-labeled LIN28A-K135R mutation is over-expressed, using anti-LIN28A-K135-me1 antibody. It was confirmed that the mono-methylated LIN28A was detected by using anti-LIN28A-K135-me1 antibody. Beta-actin was used as a loading control.

FIG. 3 shows experimental results related to binding of LIN28A and SET7/9.

FIG. 3A shows immunoprecipitation results of endogenous LIN28A derived in NCCIT cell line and SET7/9. Cell lysates were subjected to immunoprecipitation with anti IgG or anti LIN28A at 4° C. Reverse-immunoprecipitation of SET7/9 was also performed. The immunoprecipitated samples were separated by SDS-PAGE and subjected to immunoblot with IB antibodies shown in the right side of the drawing.

FIG. 3B: HEK293T cells were transfected with a vector expressing the FLAG-SET7/9 and HA-LIN28A and cultured for 48 hours to obtain cell lysates. Then, the cell lysates were immunoprecipitated in anti-FLAG agarose at 4° C. The immunoprecipitated samples were separated by SDS-PAGE and subjected to immunoblot with IB antibodies shown at the right side of the drawing.

FIG. 3C shows results obtained by culturing HEK293T cells transfected with a vector expressing HA-LIN28A as explained in FIG. 3B, and performing immunoprecipitation with LIN28A and reverse-immunoprecipitation with SET7/9.

FIG. 3D shows comparison results among K135 and other surrounding sequences in LIN28A of various animals (Hs, *Homo sapiens*; Mm, *Mus musculus*; Xl, Xenopuslaevis; Dm, *Drosophila melanogaster*; Ce, Caenorhabditiselegans). CCHC motifs were marked. Sequence comparison were performed by ClustalW2 multiple sequence alignment program (http://www.ebi.ac.uk/Tools/clustalw/index.html) and the GENEDOC software.

FIG. 4 is gene schematic diagrams of LIN28A and SET7/9 and fragments thereof.

FIG. 4A is a diagram showing full length structures of LIN28A and LIN28B and fragments of obtained proteins.

FIG. 4B is a diagram showing full length of SET7/9 protein.

FIG. 4C shows results obtained by confirming recombinant proteins produced for experiments. MAL-LIN28A, MAL-LIN28A (1-124), (69-209), (125-209), 6×HIS-LIN28A, 6×HIS-LIN28A (1-124), (69-209), (125-209), (125-156), (157-209) and 6×HIS-LIN28A-K135R were produced, and all of these were separated by SDS-PAGE, and sizes thereof were confirmed by Coomassie blue staining.

FIG. 4D shows results obtained by confirming recombinant proteins produced for experiments. GST, GST-SET7/9, GST-SET7/9 (1-207), GST-SET7/9 (208-367), MAL, MAL-SET7/9, and SET7/9 were produced, and all of these were separated by SDS-PAGE, and were confirmed by Coomassie blue staining.

FIG. 4E shows results obtained by separating recombinant human core histone (rC/H) and HeLa long oligonucleosome (LON) and performing Coomassie blue staining.

FIG. 5 shows experimental results obtained by confirming binding of SET7/9 and LIN28A in vitro.

FIGS. 5A and 5B show experimental results of in vitro pull-down assay for mapping an interacting domain. Full-length protein fused with GST, MAL, or 6×HIS, or fragments thereof were reacted at 4° C., and washed four times. Then, the bound samples were separated by SDS-PAGE, and were subjected to immunoblot with (IB) antibodies.

FIG. 5C shows results of in vitro methyltransferases assay. Recombinant full-length SET7/9 expressed in bacteria using [$^3$H] SAM as a methyl donor was reacted with full-length LIN28A or rC/H. Results obtained by radiation (above) and results obtained by Ponceau S staining (below) show methylation and protein levels, respectively. Recombinant human core histone (rC/H) was used as a positive control.

FIG. 5D shows results of in vitro methyltransferase analysis using 6×HIS-tagged LIN28A fragments. LIN28A (1-124), (125-209), (125-156), and (157-209) were tested together with SET7/9, and recombinant human core histone (rC/H) was used as a positive control.

FIG. 5E shows results of in vitro methyltransferase analysis using full-length SET7/9 of K78R, K88R, K98R, K99R, K102R, K125R, K127R, K131R, K135R, K150R and K153R in which lysine is substituted with arginine, respectively, using full-length 6×HIS-LIN28A.

FIG. 6 shows methylation results of lysine residues of LIN28B by SET7/9 and LIN28A by DOT1L.

FIG. 6A shows results of in vitro methyltransferases analysis. Recombinant full-length SET7/9 expressed in bacteria using [$^3$H] SAM as a methyl donor was reacted with full-length 6×HIS-LIN28A or -LIN28B. Results obtained by radiation (above) and results obtained by Ponceau S staining (middle) show methylation and protein levels, respectively. Recombinant human core histone (rC/H) was used as a positive control. A band concentration was measured by arbitrary units obtained by generalizing LIN28A or LIN28B methylation signal concentrations into band concentration of the used protein (below).

FIG. 6B shows results of in vitro methyltransferases analysis after reacting full-length DOT1L with full-length 6×HIS-LIN28A in Sf-21 insect cells-based baculovirus expression system. Results obtained by radiation (above) and results obtained by Ponceau S staining (below) show methylation and protein levels, respectively. LON was used as a positive control.

FIG. 7A: HEK293T cells were transfected with vectors expressing FLAG-LIN28A or FLAG-LIN28A-K135R alone or together with HA-SET7/9. After culturing for 48 hours, cell lysates were obtained and subjected to immunoblot with (IB) antibodies shown at the right side of the drawing. The error bar represents standard deviation of three independently repeated experiments (right side of the drawing).

FIG. 7B: HEK293T cells were transfected with vectors expressing FLAG-LIN28A or FLAG-LIN28A-K135R alone or together with HA-SET7/9. After culturing for 24 hours, cells were treated with 60 microgram/ml (µg/ml) of cycloheximide (CHX), and at 0, 4, 8, and 12 hours after CHX treatment, the cell lysates were recovered and subjected to immunoblot with (IB) antibodies shown at the right side of the drawing. Beta-actin was used as a loading control. Representative results obtained from three independently repeated experiments are shown in an upper panel and quantitative results graph is shown in a lower panel. Error bar represents standard deviation of three independently repeated experiments.

FIG. 7C shows results obtained by performing immunoblot on lysates of H9 cell in which HA-SET7/9 is over-expressed or endogenous SET7/9 is reduced by siRNA (100 nM). Beta-actin was used as a loading control.

FIG. 8 shows experimental results of inhibition of decomposition of LIN28A by SET7/9.

FIGS. 8A and 8B: HEK293T cells were transfected with a vector expressing FLAG-LIN28A or FLAG-LIN28A-K135R alone or together with HA-SET7/9. mRNA levels of LIN28A and SET7/9 were measured by Real-time quantitative RT-PCR (RT-qPCR). Expression levels were corrected (Normalization) with the expression level of GAPDH. Error bar represents standard deviation of three independently repeated experiments.

FIG. 8C: HEK293T cells were transfected with a vector expressing FLAG-LIN28A or FLAG-LIN28A-K135R alone or together with HA-SET7/9. After culturing cells for 24 hours, the cells were treated with 0, 20, 40, and 60 µg/ml of cycloheximide (CHX), and at 12 hours after CHX treatment, the cell lysates were recovered and subjected to immunoblot with (IB) antibodies shown at the right side of the drawing. Beta-actin was used as a loading control. Representative results obtained from three independently repeated experiments are shown in the drawing.

FIG. 8D shows immunoblot results using lysates of NCCIT cell in which HA-SET7/9 was over-expressed, or endogenous SET7/9 was decreased by siRNA (100 nM). Beta-actin was used as a loading control.

FIG. 9 shows experimental results that the methylated LIN28A is mainly present in the nucleus.

FIG. 9A: HEK293T cells were transfected with a vector expressing FLAG-LIN28A or FLAG-LIN28A-K135R. Biochemical fractions of nucleus or cytoplasm of the cell were subjected to immunoblot by (IB) antibodies shown at the right side of the drawing. H3 was used as a marker of the nucleus. α-tubulin was used as a marker of cytoplasm. As quantitative results, band concentration was expressed by an arbitrary unit (right side panel). The error bar represents standard deviation of three independently repeated experiments.

FIG. 9B: Endogenous LIN28A from biochemical fractions of the nucleus or cytoplasm of H9 cell was subjected to immunoblot by (IB) antibodies described at the right side of the drawing. H3 was used as a marker of the nucleus. α-tubulin was used as a marker of cytoplasm.

FIG. 9C: Biochemical fractions of nucleolus or nucleoplasm of H9 cell were subjected to immunoblot by (IB) antibodies described at the right side of the drawing. Fibrillarin was used as a marker of the nucleolus.

FIG. 9D shows results obtained by immunofluorescence analysis of endogenous LIN28A, LIN28A-me1, Fibrillarin, and SET7/9 of H9 cell.

FIG. 9E: The left panel is an image of immunofluorescence analysis of H9 cell in which EGFP control or SET7/9 was knocked down by siRNA. A scale bar represents 50 micrometers (µm) Immunoblot (right side panel) was performed by using lysates of H9 cell in which endogenous SET7/9 was inhibited by siRNA.

FIG. 10 shows experimental results of distribution of methylated LIN28A in NCCIT cell line.

FIG. 10A shows immunofluorescence analysis of HEK293T cells which were over-expressed with EGFP-LIN28A, EGFP-LIN28A-K135R, EGFP-SET7/9, and EGFP vectors.

FIG. 10B: Endogenous LIN28A from biochemical fractions of nucleus or cytoplasm of NCCIT cell was subjected to immunoblot by (IB) antibodies described in the right side of the drawing. H3 was used as a marker of nucleus. α-tubulin was used as a marker of cytoplasm.

FIG. 10C shows results obtained by immunofluorescence analysis of endogenous LIN28A, LIN28A-me1, and SET7/9 of the NCCIT cell. The scale bar represents 50 micrometers (μm).

FIG. 10D shows comparison analysis results between K135 and surrounding sequence of LIN28A and NoLS region sequence of LIN28B. Comparison analysis was performed by ClustalW2 multiple sequence alignment program (http://www.ebi.ac.uk/Tools/clustalw/index.html) and GENEDOC software.

FIG. 11 shows experimental results obtained by confirming that the methylated LIN28A has an activated form to inhibit processing of pri-let-7 miRNA.

FIG. 11A: HEK293T cells were co-transfected with expression vectors including human pri-let-7a-1 (primary let-7a-1) and FLAG-LIN28A, FLAG-LIN28A-K135R, or FLAG-AGO2, and the firefly luciferase gene (including let-7aBS-Luc, three binding sites of let-7a) and renilla (pRL-CMV). Relative expression levels of let-7aBS-Luc, pri-let-7a-1, and mature let-7a-1 were measured by RT-qPCR. 3' UTR of the firefly gene has three let-7a-binding sites. A signal of firefly luciferase was firstly corrected into a signal of renilla. Each value was corrected into values of GAPDH. U6 snRNA was used as a reference of mature let-7a-1 level. The error bar represents standard deviation of three independently repeated experiments.

FIG. 11B: HEK293T was co-transfected with a vector as shown in the drawing. The relative expression level of miR-16BS-Luc (having one single binding site for miR-16), pri-miR-16-1, and mature miR-16-1 was measured by RT-qPCR. Each value was corrected as shown in FIG. 11A. The error bar represents standard deviation of three independently repeated experiments.

FIG. 11C: FIG. 11C is graphs showing miRNA level changes of endogenous primary (upper panel) or endogenous mature (lower panel) let-7a family and control according to knockdown of control, LIN28A, or SET7/9 in H9 cell, measured by RT-qPCR. GAPDH and U6 snRNA were used as references of the primary and mature miRNAs, respectively.

FIG. 12 shows experimental results confirming that inhibition of processing of let-7 miRNA of LIN28A is caused by methylation signal.

FIG. 12A: As shown in the drawing, FLAG-LIN28A, FLAG-LIN28A-K135R, or FLAG-AGO2 was co-transfected in HEK293T cells together with pri-let-7a-1 with renilla and firefly luciferase gene. At 48 hours after transfection, cell lysates were subjected to immunoblot with (IB) antibodies shown at the left side of the drawing. Beta-actin was used as a loading control.

FIG. 12B: As shown in the drawing, FLAG-LIN28A or FLAG-LIN28A-K135R was co-transfected in HEK293T cells together with pri-miR-16-1 with renilla and firefly luciferase gene. At 48 hours after transfection, cell lysates were subjected to immunoblot with (IB) antibodies shown in the left side of the drawing. Beta-actin was used as a loading control.

FIG. 12C: Vectors were co-transfected in HEK293T cells as shown in the drawing. In order to measure relative expression levels of pri-let-7g, and mature let-7g, RT-qPCR was performed. GAPDH and U6 snRNA were used as references of the primary and mature miRNAs, respectively. Error bar represents standard deviation of three independently repeated experiments.

FIG. 12D: Vectors were co-transfected in HEK293T cells as shown in the drawing. The cell lysates were subjected to immunoblot with (IB) antibodies shown in the left side of the drawing. Beta-actin was used as a loading control.

FIG. 12E: As shown in the drawing, control, FLAG-LIN28A or FLAG-LIN28A-K135R was co-transfected in HEK293T cells. In order to measure LIN28A mRNA level, RT-qPCR was performed. Each expression level was corrected into expression level of GAPDH. Error bar represents standard deviation of three independently repeated experiments.

FIG. 12F shows miRNA level changes of endogenous primary (upper panel) or endogenous mature (lower panel) let-7a family and control by FLAG-LIN28A or FLAG-LIN28A-K135R in HEK293T cell, measured by RT-qPCR. GAPDH and U6 snRNA were used as references of the primary and mature miRNAs, respectively.

FIG. 13 shows experimental results confirming that pri-let-7 has affinity to a nuclear form LIN28A.

FIG. 13A shows in vitro RNA pull-down assay results. Nuclear extracts were obtained by fraction from HEK293T cells transfected with FLAG-LIN28A or FLAG-LIN28A-K135R, and reacted with let-7a-1 or miR-16-1 RNA at 4° C. S and B indicate supernatant and bead (or coupled) fraction, respectively. Quantitative results of signal of LIN28A bound to let-7a-1 were expressed by arbitrary unit of band concentration (right side panel). Error bar represents standard deviation of three independently repeated experiments.

FIG. 13B shows RNA immunoprecipitation (RIP) analysis results. As shown in FIG. 13A, biochemical fractions of nucleus and cytoplasm of the transfected HEK293T cells were subjected to RIP analysis by using antibodies shown in the drawing. All signals were corrected into input signals. Error bar represents standard deviation of three independently repeated experiments.

FIG. 14 shows experimental results confirming that LIN28A is bound to SET7/9 mRNA to facilitate translation thereof.

FIG. 14A shows RNA immunoprecipitation (RIP) analysis results. HEK293T cells were transfected with FLAG-LIN28A or FLAG-LIN28A-K135R expression vector, and RIP analysis was performed with anti-LIN28A or anti-me1 antibody. All signals were corrected into input signals. Error bar represents standard deviation of three independently repeated experiments.

FIG. 14B shows LIN28A binding motif of 3'UTR of SET7/9 and LIN28A.

FIG. 14C: HEK293T cells were transfected with control, FLAG-LIN28A or FLAG-LIN28A-K135R expression vector. mRNA level of LIN28A and SET7/9 was measured by RT-qPCR. Each expression level was corrected into expression level of GAPDH. Error bar represents standard deviation of three independently repeated experiments.

FIG. 14D: The cell lysates were subjected to immunoblot with (IB) antibodies shown in the left side of the drawing. Beta-actin was used as a loading control (left side panel). Quantitative results of SET7/9 signal were expressed by arbitrary unit of band concentration (right side panel). Error bar represents standard deviation of three independently repeated experiments.

FIG. 15A: H9 cells were transfected with control, LIN28A or SET7/9 siRNA. mRNA level was measured by RT-qPCR. Expression levels were corrected into expression levels of GAPDH. Error bar represents standard deviation of three independently repeated experiments.

FIG. 15B: H9 cells were transfected with control, LIN28A or SET7/9 siRNA. The cell lysates were separated by SDS-PAGE and subjected to immunoblot with IB antibodies shown in the right side of the drawing. Beta-actin was used as a loading control.

FIG. 15C shows quantitative comparison results of representative genes. siRNAs were transfected in H9 cells as shown in FIG. 15A. mRNA levels of early lineage markers such as WINT3 and T (related to mesoderm differentiation), GATA4 and FOXA2 (related to endoderm differentiation), and PAX6 and Nestin (related to ectoderm differentiation), and the like, were measured by RT-qPCR. Each expression level was corrected into expression level of GAPDH. Error bar represents standard deviation of three independently repeated experiments.

FIG. 16 shows experimental results confirming that nuclear form LIN28A is important to polymorphic regulation of NCCIT cell.

FIG. 16A: NCCIT cells were transfected with control, LIN28A or SET7/9 siRNA. mRNA level was measured by RT-qPCR. Expression levels were corrected into expression levels of GAPDH. Error bar represents standard deviation of three independently repeated experiments.

FIG. 16B: NCCIT cells were transfected with control, LIN28A or SET7/9 siRNA. The cell lysates were separated by SDS-PAGE and subjected to immunoblot with IB antibodies shown in the right side of the drawing. Beta-actin was used as a loading control.

FIG. 16C shows quantitative comparison results of representative genes. siRNAs were transfected in NCCIT cells as shown in FIG. 16A. mRNA levels of early lineage markers were measured by RT-qPCR. Each expression level was corrected into expression level of GAPDH. Error bar represents standard deviation of three independently repeated experiments.

FIG. 17 shows experimental results of expression profile in hESC from which LIN28A and SET7/9 are deficient.

FIG. 17A is MA plot of LIN28A- or SET7/9-siRNA vs EGFP-siRNA of twice repeated microarray experiment. M and A axes indicate log values of concentration (multiple changes), and an average log concentration, respectively. Red dots indicate transcriptomes changed by three times or more as compared to control (EGFP-siRNA) due to knockdown of LIN28A or SET7/9 in each repeated experiment.

FIG. 17B is scatter plot showing comparison between LIN28A-siRNA (x-axis) and SET7/9-siRNA (y-axis) in view of gene expression changes ($\log_2$ ratio) in each repeated experiment.

FIG. 17C is a biological process in view of gene ontology related with genes changed by LIN28A- or SET7/9-siRNA. Genes changed by three times or more in both repeated experiments were selected.

FIG. 17D is graphs showing expression level comparison of representative early lineage markers of hESC from which LIN28A and SET7/9 determined by microarray analysis are deficient. FIG. 17D shows multiple ($\log_2$) of changed values and expression level of genes having high score.

FIG. 18 shows experimental results of gene set analysis of differently expressed genes and expression change of let-7 target gene.

FIGS. 18A, 18B, and 18C: The drawings show biological process in view of gene ontology (GO) in which genes having three times or more of changes due to knockdown by LIN28A-siRNA and SET7/9-siRNA are involved. Top 20 GO biological processes are represented for each group.

FIG. 18D is an expression level graph of let-7 target genes in hESC from which LIN28A and SET7/9 determined by microarray analysis are deficient. FIG. 18D shows multiple ($\log_2$) of changed values and expression profile of let-7 target gene.

ADVANTAGEOUS EFFECTS

Figure 2:
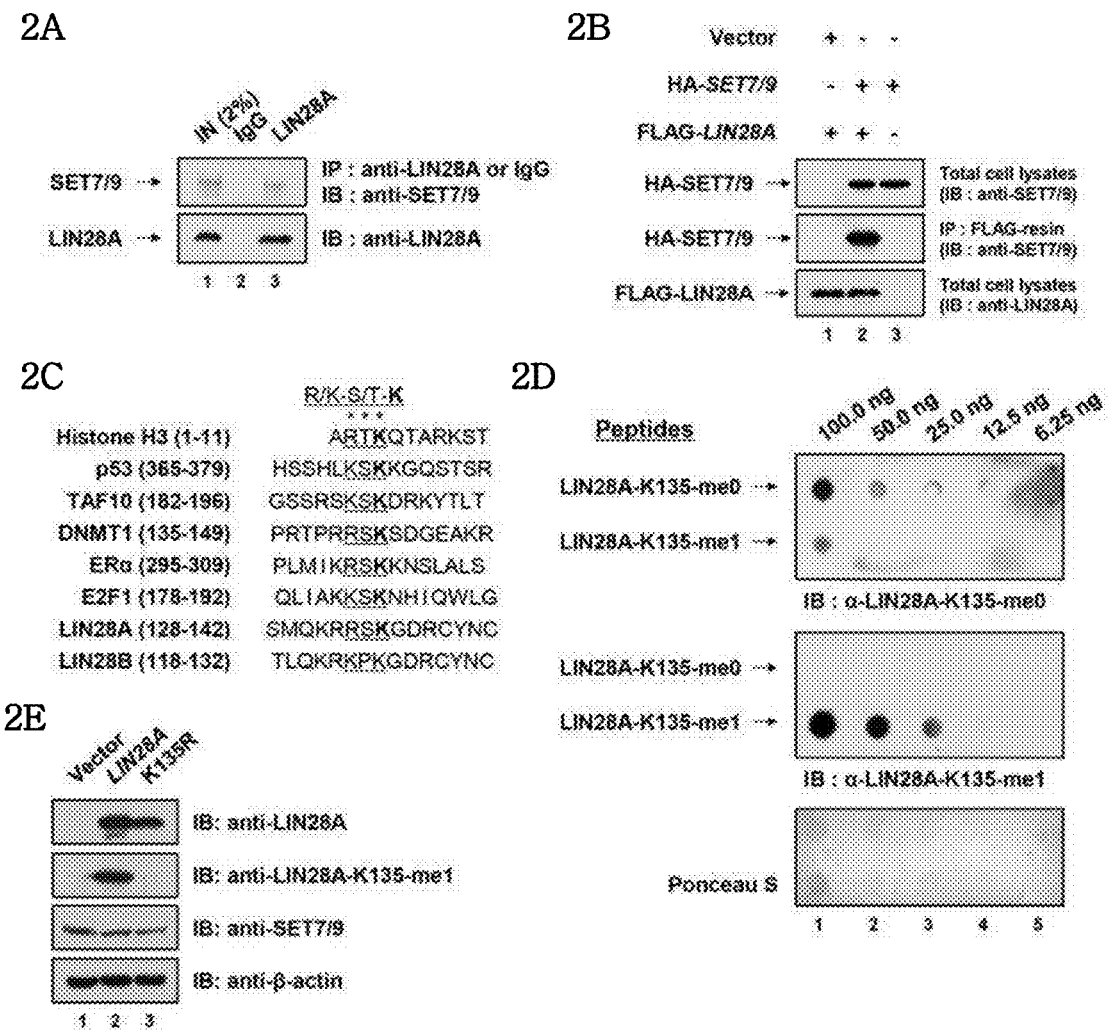
FIG. 2 shows experimental results of relevance of LIN28A methylation and SET7/9.

As set forth above, the method of the present invention is possible to effectively screen materials capable of controlling pluripotency of embryonic stem cells or materials having anti-cancer activity, and the materials screened by the method of the present invention may control pluripotency of embryonic stem cells and inhibit growth of cancer cells, which is effective for disorders of stem cell differentiation or preparation of therapeutic cancer agents.

BEST MODE

As it is not defined in other ways, all technical and scientific terms used in the present specification have the same meaning as being generally appreciated by those skilled in the art to which the present invention pertains. In general, the nomenclature used in the present specification is well known in technical fields and generally used.

Term "stem cell" used herein means a cell having excellent proliferation ability and being possible to be differentiated into various body tissues.

Pluripotency refers to differentiation potency of all cells of fetus or adult, and pluripotent stem cells are cells before early embryo cells are divided and differentiated into various organs, and may be proliferated indefinitely in vitro in an undifferentiated state, and these cells are possible to be differentiated into various organs such as heart, pancreas, liver, skin, nerve, and the like.

MicroRNA (hereinafter, referred to as "miRNA") is produced from hairpin RNA forming a partial double-helix, and specifically bound specific messenger RNA (mRNA) to inhibit processing in which protein is generated from mRNA, thereby controlling expression of many genes.

In particular, a strong relationship between miRNA and cancer has recently demonstrated and emerged as a new research topic in cancer biology (Esquela-Kerscher, A. and Slack, F. J., (2006) Nat. Rev. Cancer 6(4):259-269), and as expression of miRNA is dramatically changed in development and cell differentiation processing, such that profiling of miRNA has shown reliable results in the development system and disease stage (Lu, J. et al., (2005) Nature 435:834-838).

let-7 miRNA is one of miRNA, and related to generation of embryo, occurrence of cancer cell, and the like. When the let-7 miRNA is not normally created or does not properly function, problem may occur in an embryonic development process, and cancer may be developed. U.S. Patent Laid-Open Publication No. 2006/0189557 discloses a method for treating cancer by introducing let-7 miRNA into a cancer cell to inhibit activity of RAS oncogene.

LIN28A is a conserved RNA-binding protein, and an expression thereof is strictly regulated in an animal developmental process. LIN28A plays an important role in the generation and particular diseases. For example, LIN28A is highly expressed in embryonic stem cells, and is one of four factors required for changing fibroblasts of human or mice into induced pluripotent stem cells (iPSCs).

A mechanism in which LIN28A is activated in the nucleus has not been found so far. The present inventors found that LIN28A of which the $135^{th}$ lysine is methylated is stably present in the nucleus, inhibits processing of the pri-let-7 miRNA to control cell potency and differentiation potency and inhibits mature let-7 level related with cancer inhibition. The above description has just been revealed for the first time.

Accordingly, it may be appreciated that a material inhibiting a methylation level of $135^{th}$ lysine of LIN28A is capable of normalizing pluripotency of embryonic stem cells, and inhibiting the occurrence of cancer cells.

SET7/9 is referred to as SETD7, and is methyltransferase which methylates histone H3 and p53, TAF 10, non-histone proteins such as estrogen receptor alpha. SET7/9 is found mainly in active chromatin. It is currently known that SET7/9 is a major post-translation modifier and controls activity of non-histone protein as well as histone protein.

The present inventors studied the above-described methylation mechanism of LIN28A, and found that methylation of $135^{th}$ lysine of LIN28A is due to SET7/9, specifically, direct bonding between SET7/9 and LIN28A. The above description in the present invention has just been revealed for the first time.

Accordingly, it may be appreciated that a material affecting a binding level of LIN28A and SET7/9 is capable of normalizing pluripotency of embryonic stem cells, and inhibiting occurrence of cancer cells.

Therefore, the present invention is to provide a composition for controlling pluripotency of embryonic stem cells including an inhibitor controlling methylation of $135^{th}$ lysine of LIN28A that is methylated by SET7/9.

In addition, the present invention is to provide a composition for preventing or treating cancer, including an inhibitor controlling methylation of $135^{th}$ lysine of LIN28A that is methylated by SET7/9.

The "inhibitor" of the present invention is any material as long as it inhibits methylation of $135^{th}$ lysine of LIN28A, or inhibits biding level of LIN28A and SET7/9, preferably, a material that is applicable to a living body. For example, the inhibitor may be LIN28A or SET7/9-specific antibodies or aptamer; RNAi that interferes expression of LIN28A or SET7/9; miRNA that inhibits expression of LIN28A or SET7/9; and a natural compound or a synthetic compound that inhibits expression of LIN28A or SET7/9, but is not limited thereto.

Preferably, it may be siRNA consisting of sequence of SEQ ID NO: 3 or SEQ ID NO: 4 as a sense strand and complementary sequence thereof as an antisense strand.

In addition, the present invention provides a screening method of a material for inhibiting pluripotency of embryonic stem cells, the screening method including: (a) contacting a candidate material with a cell, the cell having a LIN28A gene introduced thereinto; (b) measuring a methylation level of $135^{th}$ lysine of the LIN28A; and (c) selecting an inhibitor controlling methylation of the $135^{th}$ lysine of the LIN28A.

Further, the present invention provides a screening method of a material for inhibiting pluripotency of embryonic stem cells, the screening method including: (a) contacting a candidate material with a cell, the cell having a LIN28A gene introduced thereinto; (b) measuring a binding level of LIN28A and SET7/9; and (c) selecting an inhibitor controlling the binding level of LIN28A and SET7/9.

In addition, the present invention provides a screening method of an anti-cancer material, the screening method including: (a) contacting a candidate material with a cell, the cell having a LIN28A gene introduced thereinto; (b) measuring a methylation level of $135^{th}$ lysine of the LIN28A; and (c) selecting an inhibitor controlling methylation of the $135^{th}$ lysine of the LIN28A.

Further, the present invention provides a screening method of an anti-cancer material, the screening method including: (a) contacting a candidate material with a cell, the cell having a LIN28A gene introduced thereinto; (b) measuring a binding level of LIN28A and SET7/9; and (c) selecting an inhibitor controlling the binding level of LIN28A and SET7/9.

LIN28A was first discovered in a nematode C. elegans, and proteins from worm to human are homologues. The embryonic stem cell of the present invention is not specifically limited in view of origin thereof, for example, may be derived from all symmetrical animals (Bilateria) including protostomia and deuterostomia, preferably, may be derived from chordatam, more preferably, may be derived from mammalian, and the most preferably, may be a human embryonic stem cell derived from human.

The 'material' of the method of the present invention is any material as long as it inhibits methylation of $135^{th}$ lysine of LIN28A, or inhibits a binding level of LIN28A and SET7/9, preferably, a material that is applicable to a living body. For example, the material may be selected from natural compounds, synthetic compounds, DNA, RNA, peptides, enzymes, ligands, cell extracts and secretions of the mammalians, but is not limited thereto.

Preferably, it may be selected from the group consisting of LIN28A or SET7/9-specific antibodies or aptamer; RNAi that interferes expression of LIN28A or SET7/9; miRNA that inhibits expression of LIN28A or SET7/9; and a natural compound or a synthetic compound that inhibits expression of LIN28A or SET7/9.

The cell having a LIN28A gene introduced thereinto of the method of the present invention is any cell as long as LIN28A gene is capable of being introduced and expressed, preferably, a stem cell, and more preferably, H9, HEK293T or NCCIT cell.

HEK293T cell refers to a human fetus kidney cells. H9 cell is a derivative of Hut 78 cell line (ATCC TIB-161) and one kind of a human embryonic stem cell. NCCIT cell (ATCC CRL-2073) is a nonseminomatous germ cell tumor-derived stem cell line, and a hybrid of seminoma and embryonal carcinoma.

In an exemplary embodiment of the present invention, an enzyme that methylates LIN28A was confirmed. As a result, it was confirmed that SET7/9 among various methylation enzymes exhibits enzyme activity with respect to LIN28A.

In another exemplary embodiment of the present invention, whether LIN28A and SET7/9 directly react in vivo was confirmed by pull-down assay. As a result, direct reaction of LIN28A and SET7/9 was confirmed.

In other exemplary embodiment of the present invention, four different fragments of LIN28A were independently expressed, and measured methylation by SET7/9, in order to confirm positions at which LIN28A is methylated by SET7/9. As a result, it was confirmed that only fragment having $135^{th}$ lysine (K135) of LIN28A was methylated.

In another exemplary embodiment of the present invention, mutants in which various lysines including K135 in LIN28A are substituted with arginines (R) each having the same charge as each other but not being methylated by SET7/9 which is a lysine specific methylation enzyme are produced and whether or not the methylation by SET7/9 is achieved was confirmed. As a result, it was confirmed that the methylation reaction by SET7/9 was completely removed from K135 mutant, and therefore, it was confirmed that SET7/9 allowed lysine 135 of LIN28A to be methylated.

In another exemplary embodiment of the present invention, an intracellular level of the methylated LIN28A was measured to confirm an effect of methylation of LIN28A. As a result, it was confirmed that intracellular stability of the methylated LIN28A was improved and half-life thereof was increased.

In another exemplary embodiment of the present invention, intracellular distribution of the methylated LIN28A was measured. As a result, it was confirmed that the methylated LIN28A was present in a nucleus, in particular, nucleolus.

In another exemplary embodiment of the present invention, pri-let-7 miRNA processing by the methylated LIN28A was confirmed to confirm property of the methylated LIN28A. As a result, it was confirmed that inhibition of the pri-let-7 miRNA processing was generated by LIN28A.

In another exemplary embodiment of the present invention, it was confirmed that the methylation of LIN28A was inhibited by a method of using LIN28A or siRNA targeting SET7/9 to induce knockdown of LIN28A or SET7/9 in H9 human embryonic stem cells.

As a result, it was confirmed that when the methylation of LIN28A was inhibited, inhibition of pri-let-7 miRNA processing enhanced by the methylated LIN28A was overcome to accumulate mature let-7.

In addition, as a result obtained by analyzing change in transcription expression profiling by the methylated LIN28A, it was confirmed that expression of an early lineage marker was increased by inhibition of the methylated LIN28A, and the methylated LIN28A specifically controlled let-7 miRNA to perform important functions in controlling cell potency and differentiation potency.

As described above, a material inhibiting the methylation of $135^{th}$ lysine of LIN28A or inhibiting the binding level of LIN28A and SET7/9 may control pluripotency of embryonic stem cells or may control occurrence of a cancer cell.

The composition of the present invention includes an inhibitor obtained by the screening method of the present invention as an effective ingredient.

A pharmaceutical composition according to the present invention may include the material of the present invention alone, or may further include one or more pharmaceutically acceptable carriers. The "pharmaceutically effective amount" refers to an amount exhibiting reaction larger than that of a negative control group, preferably, an amount sufficient to treat cancer.

The term "pharmaceutically acceptable" means a non-toxic composition that is physiologically acceptable, and does not inhibit action of active ingredients, and generally does not cause allergic reactions such as gastrointestinal disorders, dizziness, or similar reactions when being administered to a human.

The cancer is not specifically limited in view of a kind, for example, the cancer may be colon cancer, lung cancer, small cell lung cancer, stomach cancer, liver cancer, blood cancer, bone cancer, pancreatic cancer, skin cancer, head or neck cancer, cutaneous or intraocular melanoma, uterine cancer, ovarian cancer, rectal cancer, anal cancer, colorectal cancer, breast cancer, fallopian tube carcinoma, endometrial carcinoma, cervical cancer, vaginal cancer, vulva carcinoma, Hodgkin's disease, esophageal cancer, small intestine cancer, endocrine cancer, thyroid cancer, parathyroid cancer, adrenal cancer, soft tissue sarcoma, urethral cancer, penis cancer, prostate cancer, chronic or acute leukemia, lymphocyte lymphoma, bladder cancer, kidney or ureter cancer, renal cell carcinoma, renal pelvis carcinoma, CNS tumor, primary CNS lymphoma, spinal cord tumor, brain stem glioma, and pituitary adenoma.

In the pharmaceutical composition according to the present invention, when being clinically administered, the material may be administered in a variety of oral and parenteral dosage forms, and when being formulated, the material may be prepared with generally used diluents or excipients such as a filler, an extender, a binder, a wetting agent, a disintegrant, a surfactant, and the like.

Solid formulation for oral administration includes tablets, pills, powders, granules, capsules, troches, and the like, and may be prepared with at least one excipient such as starch, calcium carbonate, sucrose, lactose, gelatin, or the like. In addition, lubricants such as magnesium stearate, talc, and the like, may also be used, in addition to simple excipients. Liquid formulations for oral administration include suspensions, solutions, emulsions, syrups, and the like, and may include various excipients, for example, wetting agents, sweeteners, aromatics, preservatives, and the like, in addition to generally used simple diluents such as water, liquid paraffin, and the like.

Preparations for parenteral administration include sterile aqueous solution, non-aqueous solvent, suspending solvent, emulsion, freeze drying preparation, suppository, and the like.

A therapeutic composition of the present invention may be prepared in a lyophilized cake or an aqueous solution for storing a mixture containing any physiologically acceptable carriers, excipients, or stabilizers (Remington: The Science and Practice of Pharmacy, 19th Edition, Alfonso, R., Ed, Mack Publishing Co. (Easton, Pa.: 1995) with the material of the present invention having preferable purity. The allowable carrier, excipient, or stabilizer is non-toxic to recipients at the used dosage and concentration, and may include a buffer solution such as phosphoric acid, citric acid and other organic acids; an antioxidant including ascorbic acid; a low molecular (less than about 10 residues) polypeptide; a protein such as serum albumin, gelatin or immunoglobulin; a hydrophilic polymer such as polyvinylpyrrolidone; an amino acid such as glycine, glutamine, asparagine, arginine or lysine; monosaccharide, disaccharide, and glucose, other carbohydrates including mannose or dextrin; a chelating agent such as EDTA; sugar alcohol such as mannitol or sorbitol; salt-forming counterion such as sodium; and (or) non-ionic surfactant such as Tween, pluronics or polyethylene glycol (PEG).

In addition, dosage of the material of the present invention for each human may vary depending on the patient's age, weight, sex, dosage form, health state and disease extent. Generally, the dosage may be 0.01-100 mg/kg/day, preferably 0.1-20 mg/kg/day. In addition, the dosage may be division-administered once a day to several times at a predetermined time interval according to the judgment of a doctor or pharmacist.

An administration route of the composition of the present invention includes known methods, for example, injection or infusion by intravenous, intraperitoneal, brain, subcutaneous, intramuscular, intraocular, intraarterial, cerebrospinal or lesion paths, or injection or infusion by sustained release system. Preferably, the composition of the present invention may be administered in a systemic way.

The pharmaceutical composition of the present invention may be used alone for prevention or treatment of cancer, or may be used in combination with surgery, hormone therapy, chemical therapy, and methods of using biological response modifiers.

EXAMPLE

Hereinafter, the present invention will be described in detail with reference to the following Examples. However, the following examples are only for exemplifying the present invention, and it will be obvious to those skilled in the art that the scope of the present invention is not construed to be limited to these examples. Therefore, the substantial scope of the present invention is defined by the accompanying claims and equivalent thereof.

<Experimental Method>

Methods used for experiments are as follows.

Cell Line

Human embryonic stem cells were cultured as described in the existing reports (Rho et al., (2006) Hum Reprod 21, 405-412). Briefly, H9 cells were cultured with mouse embryonic fibroblast (mct-MEFs) treated with mitomycin C (Sigma, St Louis, Mo.) in an embryonic stem cell culture medium in which 4 ng/ml of a basic fibroblast growth factor (Invitrogen, Carlsbad USA), 0.1 mM β-mercaptoethanol (Sigma, USA) were added to Dulbecco modified Eagle medium (DMEM)/F12 medium (Invitrogen, Carlsbad, Calif.) containing 20% knockout serum replacement, 1% non-essential amino acid, 1% penicillin-streptomycin (Invitrogen) under conditions of 37° C. and 5% $CO_2$.

NCCIT cell and HEK293T cell were cultured in RPMI 1640 (Gibco) and DMEM (Hyclone) containing 10% fetal bovine serum (FBS, Hyclone) and 1% antibiotic-antimycotic solution (Hyclone), respectively, under conditions of 37° C. and 5% $CO_2$.

In Vitro Analysis of Methyl Transferase

In vitro analysis of methyl transferase was performed as described in the existing reports (Shi et al., (2006) Nature 442, 96-99). Briefly, recombinant human-methyl transferase was obtained by purification from bacterial expression system, and recombinant full-length DOT1L protein was obtained from baculovirus expression system (Kim et al., (2013) J BiolChem 287, 39698-39709). 500 ng of each of purified recombinant target protein, recombinant human core histone (rC/H), or HeLa long oligonucleosomes (LON) was dissolved in 20 ul of a solution containing 50 mM Tris-HCl (pH 8.0), 5% glycerol, 20 mM KCl, 5 mM $MgCl_2$, 1 mM dithiothreitol, 1 mM PMSF, 1 micro curie (uCi) [$^3$H] methyl S-adenosyl-methionine ([$^3$H] SAM; 1 uCi, Amersham Biosciences) and allowed to stand at 30° C. for 3 hours.

Then, SDS buffer was added to stop the reaction, the products were separated by 14% SDS-PAGE, and results thereof were confirmed by radiography.

Protein Purification and In Vitro Pull-Down Assay

GST and GST fusion proteins were expressed in *E. coli* (Rosetta 2) and purified, and performed in accordance with partially modified instructions of the manufacturer (Novagen). Briefly, expression of GST and GST-fusion proteins was induced by 0.5 mM IPTG (Isopropyl-β-d-thiogalactopyranoside) at 37° C. for 3 hours for a small amount of purification, and recovered cells were re-suspended in cell lysis/washing buffer (40 mM HEPES-NaOH, pH 7.4, 350 mM NaCl, 10% (v/v) glycerol, 0.1% Tween-20, 1 mM PMSF/Protease inhibitors), followed by sonication. Then, clear cells obtained by centrifugation under conditions of 14,000 rpm and 4° C. for 20 minutes were reacted with glutathione-Sepharose 4B beads (GE Healthcare) at 4° C. for 2 hours. The beads bound to the protein were strongly washed three times with cell lysis/washing buffer, and GST-fusion protein was eluted with GST elution buffer (100 mM Tris-Cl, pH 8.0, 20 mM Glutathion) and dialyzed with dialysis buffer (25 mM Tris-Cl, pH 8.0, and 20% (v/v) glycerol). The purified protein was used for in vitro pull-down assay. MBP and MBP fusion protein were expressed by the above-described method, and were purified by using MAL elution buffer (20 mM Tris-Cl, pH 7.5, 200 mM NaCl, 10 mM Maltose, 1 mM ethylene diaminetetraacetic acid (EDTA) (New England Biolabs, Inc.) in accordance with manufacturer's instructions. 6×HIS-fusion protein was expressed by the above-described method, and was washed with TALON lysis/washing buffer (8 M Urea, 50 mM sodium phosphate, pH 7.0, 300 mM NaCl, 1 mM PMSF/Protease inhibitors). Then, the product was eluted with TALON elution buffer (7.2 M Urea, 45 mM sodium phosphate, pH 7.0, 270 mM NaCl, 150 mM Imidazole), and dialyzed with dialysis buffer I (1 M Urea, 50 mM Tris-Cl, pH 10.5, 200 mM NaCl, 5% (v/v) glycerol) and dialysis buffer II (5 mM Tris-Cl, pH 8.0, 150 mM NaCl, 5% (v/v) glycerol) in accordance with manufacturer's instructions (Clontech).

The purified GST fusion protein, MAL fusion protein, 6×HIS fusion protein were added to a pull-down buffer (50 mM HEPES, pH 7.4, 10% glycerol, 1 mM EDTA, pH 8.0, 150 mM NaCl, 0.1% Tween-20, 20 mM β-mercaptoethanol, 1 mM PMSF/Protease inhibitors) and reacted for 1 hour at 4° C. Then, glutathione-Sepharose 4B beads or amylose resin (New England Biolabs, Inc.) were added thereto and reacted for 1 hour, and then the bound protein complexes were washed four times with a binding buffer, separated by SDS-PAGE, and analyzed by an immunoblot method.

Immunoprecipitation and Western Blot Analysis Method

HEK293T was transformed by TurboFect in vitro (Thermo), and a plasmid used for transformation was obtained from Qiagenminiprep procedure (Qiagen). After 24 hours for transformation, transformed HEK293T or H9 and untransformed NCCIT were cell-lysed with EBC buffer (50 mMTris-HCl, pH 7.5, 150 mM NaCl, 0.5% NonidetP-40, 50 mM NaF, 200 uM sodium orthovanadate, and 1 mM PMSF/Protease inhibitors), and were stirred with FLAG M2 agarose beads (Sigma-Aldrich, A2220) or corresponding antibodies and a protein G-agarose (GE Healthcare) mixture, and reacted at 4° C. for 3 hours. The precipitated protein complex was washed three times with EBC buffer, and added to SDS buffer and boiled for 5 minutes to perform separation by SES-PAGE. Then, immunoblot method was performed for analysis.

Antibody

Antibodies used to recognize LIN28A-K135-me0, LIN28A-K135-me1, and H3 were polyclonal rabbit antibodies produced in the laboratory as described in previous document (Kim et al., (2013) J BiolChem 287, 39698-39709; Oh et al., (2010) BiochemBiophys Res Commun 399, 512-517). For LIN28A (Cell signaling, 5930S), SET7/9 (Santa Cruz Biotechnology, sc-56774), GST (Santa Cruz Biotechnology, sc-138), α-tubulin (Cell signaling, 2144), FLAG (Sigma-Aldrich, F1804), β-actin (Santa Cruz Biotechnology, sc-47778), OCT4 (Santa Cruz Biotechnology, sc-9081), NANOG (Cell signaling, 3580), SOX2 (Cell signaling, 3579), and Fibrillarin (Abcam, ab18380), commercially available antibodies were used. Dot blot analysis was performed by making dots with LIN28A-K135-me0 or LIN28A-K135-me1 peptide on nitrocellulose membrane, and using α-LIN28A-K135-me0 or LIN28A-K135-me1 antibody.

Immunofluorescence

Cells were fixed with 4% formaldehyde (Sigma-Aldrich, HT5011) for 20 minutes, washed with PBST (PBS containing 0.1% Tween 20; Sigma-Aldrich, P7949) 3 times for 15 minutes, and reacted with PBS containing 0.1% Triton X-100 (Sigma-Aldrich, T8532) and with blocking solution (3% fetal bovine serum; Sigma-Aldrich, A9647) at room temperature for 1 hour. Primary antibodies of LIN28A, LIN28A-K135-me1, SET7/9, Fibrillarin diluted at 1:200 in a blocking solution were reacted with cells overnight at 4° C., and washed six times with PBST, and reacted with secondary antibodies (Invitrogen) bound with Alexa-488- or -594-diluted at 1:300 in a blocking solution under dark condition at room temperature for 1 hour, and washed six times with PBST. During the washing process, DNA was contrast-stained with DAPI (4'-6-diamidino-2-phenylindole Sigma-Aldrich, D5942). Lastly, Zeiss LSM 510 confocal microscope (Carl Zeiss, Germany) equipped with argon and helium-neon lasers was used to obtain fluorescent image.

RNA Isolation and Reverse Transcription (RT) Test

H9, NCCIT, or HEK293T cells were subjected to duplicate culture, and total RNA was isolated by using TRIZOL® Reagent (Invitrogen) in accordance with the manufacturer's instructions. Briefly, cells cultured in a petri dish with a diameter of 35 mm were recovered, 500 ul of TRIZOL was added thereto, and cell elution passed through a pipette several times for homogenization, and allowed to stand at 25° C. for 5 minutes so as to completely separate nuclear protein complex. 100 ul of chloroform was added thereto, and shaken strongly for 15 seconds to be mixed, and allowed to stand at 25° C. for 2-3 minutes. centrifugation was performed at 12,000×g and 4° C. for 15 minutes, and only the supernatant was transferred to a new tube. In order to leach RNA, 200 ul of isopropyl alcohol was added and mixed with each other, and reacted at 25° C. for 10 minutes. The resultant mixture was centrifuged at 12,000×g, and 4° C. for 15 minutes, and washed with 75% ethanol, and RNA sediment was dried and eluted in RNase-free water. cDNA was synthesized from total RNA treated with 1 µg of DNase by using Improme Kit (Promega) in accordance with the manufacturer's instruction.

Real-Time Quantitative RT-PCR

CFX96 (Bio-Rad) was used for real-time PCR analysis. In order to amplify DNA, 2×h-Taq real time mix (Solgent), 20× Evagreen (Biotium), 20× tetraethylammonium chloride, 10 pmol of each primer and a template DNA were mixed with each other. The obtained mixture was taken in total volume of 20 ul and used for reaction. PCR reaction was performed by an initial stage of 95° C. for 12 minutes, and 40 times repetition of the following processes: 20 seconds at 95° C. (denaturation), 30 seconds at 57° C. (annealing), 30 seconds at 72° C. (extension), and final stage of 5 minutes at 72° C. Specificity of the primer used in the PCR was confirmed by agarose gel electrophoresis. After PCR was performed, a melting curve was analyzed to determine amplification of a single PCR product, and Ct (threshold cycle) was determined in each reaction. Average Ct values for 2 copies of IP DNA and added DNA in three PCR reactions were shown as A and B, respectively. Fold enrichment (F) values (F=½^(A−B)) for each IP sample were calculated and compared with GAPDH, and relative mRNA expression amount was calculated.

Primer sequences used for real-time PCR analysis consisted of SEQ ID NOS: 6 to 50, and detailed sequences are shown in Table 1 below.

TABLE 1

Primer Sequences for Real-time PCR anlaysis

| SEQ ID NO: | Name | Type | Sequence |
|---|---|---|---|
| 6 | LIN28A-RT-F | DNA | AGCATGCAGAAGCGCAGATCAA |
| 7 | LIN28A-RT-R | DNA | GCTACCATATGGCTGATGCTCT |
| 8 | SET7/9-RT-F | DNA | TCATTGATGTGCCTGAGCCCTA |
| 9 | SET7/9-RT-R | DNA | TCAGGGTGCGGATGCATTTGAT |
| 10 | OCT4-RT-F | DNA | AAACCCACACTGCAGCAGATCA |
| 11 | OCT4-RT-R | DNA | TCGTTGTGCATAGTCGCTGCTT |
| 12 | SOX2-RT-F | DNA | TGTGGTTACCTCTTCCTCCCACT |
| 13 | SOX2-RT-R | DNA | TGGTAGTGCTGGGACATGTGAA |
| 14 | NANOG-RT-F | DNA | ACCTTCCAATGTGGAGCAACCA |
| 15 | NANOG-RT-R | DNA | TGCATGCAGGACTGCAGAGATT |
| 16 | GAPDH-RT-F | DNA | ACATCAAGAAGGTGGTGAAGCAGG |
| 17 | GAPDH-RT-R | DNA | CACCCTGTTGCTGTAGCCAAAT |
| 18 | Firefly-RT-F | DNA | CGAAGGTTGTGGATCTGGATA |
| 19 | Firefly-RT-R | DNA | CGCTTCCGGATTGTTTACATA |
| 20 | Renilla-RT-F | DNA | TTATCATGGCCTCGTGAAATC |
| 21 | Renilla-RT-R | DNA | CTGGGTCCGATTCAATAAACA |
| 22 | Pri-let-7a-1-RT-R | DNA | GATTCCTTTTCACCATTCACC |
| 23 | Pri-let-7a-1-RT-F | DNA | TTTCTATCAGACCGCCTGGAT |
| 24 | Pri-let-7g-RT-R | DNA | CCTGTCTCAAGTGCATCCTG |
| 25 | Pri-let-7g-RT-F | DNA | CAGAGATGAGCAGGGTGACG |
| 26 | Pri-miR-16-1-RT-R | DNA | AGGTGCAGGCCATATTGTGCT |
| 27 | Pri-miR-16-1-RT-F | DNA | CTGAAAAGACTATCAATAAAAC |
| 28 | Mature let-7a-RT-F | DNA | TGAGGTAGTAGGTTGTATAGTT |
| 29 | Mature let-7b-RT-F | DNA | TGAGGTAGTAGGTTGTGTGGTT |
| 30 | Mature let-7c-RT-F | DNA | TGAGGTAGTAGGTTGTATGGTT |
| 31 | Mature let-7d-RT-F | DNA | AGAGGTAGTAGGTTGCATAGTT |
| 32 | Mature let-7e-RT-F | DNA | TGAGGTAGGAGGTTGTATAGTT |
| 33 | Mature let-7f-RT-F | DNA | TGAGGTAGTAGATTGTATAGTT |
| 34 | Mature let-7g-RT-F | DNA | TGAGGTAGTAGTTTGTACAGTT |
| 35 | Mature let-7i-RT-F | DNA | TGAGGTAGTAGTTTGTGCTGTT |
| 36 | Mature miR-98-RT-F | DNA | TGAGGTAGTAAGTTGTATTGTT |
| 37 | Mature miR-16-RT-F | DNA | TAGCAGCACGTAAATATTGGCG |
| 38 | Mature miR-21-RT-F | DNA | CAACACCAGTCGATGGGCTGT |
| 39 | WINT3-RT-F | DNA | GGCCATGAACAAGCACAACA |
| 40 | WINT3-RT-R | DNA | TGCCGTGGGAGGTGACATT |

TABLE 1-continued

Primer Sequences for Real-time PCR analysis

| SEQ ID NO: | Name | Type | Sequence |
|---|---|---|---|
| 41 | T (Brachyury)-RT-F | DNA | GCGGGAAAGAGCCTGCAGTA |
| 42 | T (Brachyury)-RT-R | DNA | TTCCCCGTTCACGTACTTCC |
| 43 | GATA4-RT-F | DNA | TCCAAACCAGAAAACGGAAG |
| 44 | GATA4-RT-R | DNA | CTGTGCCCGTAGTGAGATGA |
| 45 | FOXA2-RT-F | DNA | CTGAGCGAGATCTACCAGTGGA |
| 46 | FOXA2-RT-R | DNA | AGTCGTTGAAGGAGAGCGAGT |
| 47 | PAX6-RT-F | DNA | GTGTCCAACGGATGTGTGAG |
| 48 | PAX6-RT-R | DNA | CTAGCCAGGTTGCGAAGAAC |
| 49 | NES (Nestin)-RT-F | DNA | AAGAAATAAATCAGGGGCA |
| 50 | NES (Nestin)-RT-R | DNA | CAGGTTCTCTTCCTCTTCCA |

Ultracentrifugation Cell Fractionation Experiment

Nuclear extracts were prepared by partially modified methods from the existing document (Kim et al., (2013) J BiolChem 287, 39698-39709). H9 or HEK293T cells were recovered and washed with cold PBS twice, and then 5× extraction buffer I (10 mM HEPES, pH 7.9, 1.5 mM $MgCl_2$, 10 mMKCl, and 1 mM PMSF/Protease inhibitors) was added and mixed well, followed by vortex for 15 seconds, and placed on ice for 10 minutes. 10% NP-40 was added to have a final concentration of 0.9%, followed by vortex for 15 seconds, and placed on ice for 5 minutes. Each sample was centrifuged at 4° C., 5000 rpm for 5 minutes to precipitate cell nucleus, and supernatant was completely removed. Precipitated nucleus was washed with extraction buffer I twice, and then extraction buffer II (20 mM HEPES, pH 7.9, 150 mM NaCl, 1.5 mM $MgCl_2$, 0.2 mM EDTA, 1 mM PMSF/Protease inhibitors) was added and mixed well, followed by vortex for 20 seconds, and placed on ice for 40 minutes. Cell nucleus suspension was subjected to vortex for 10 seconds, passed through 23-G injection needle 4-6 times for homogenization, followed by centrifugation at 4° C., 14,000 rpm for 15 minutes. The supernatant was used as cell nucleus extract and RNA in vitro pull-down assay and RNA immunoprecipitation method were performed.

Nucleolus was prepared by partially modified methods from the existing document (Piskounova et al., (2011) Cell 147, 1066-1079). Cell nucleus was treated with extraction buffer II (with 420 mM NaCl), and rotation-stirred at 4° C. for 30 minutes, and centrifuged at 12,000 rpm for 30 minutes to precipitate the nucleolus. Extraction buffer III (50 mM Tris-Cl, pH 7.9, 25% glycerol, 5 mM $MgCl_2$, 0.5 mM EDTA) was added to the precipitated nucleolus to be resuspended, and the obtained product was passed through 23-G needle 4-6 times for homogenization, followed by centrifugation to separate soluble or insoluble fractions. Nucleolus precipitated fractions were re-suspended with extraction buffer IV (20 mM Tris-Cl, pH 8.0, 10% Glycerol, 137 mM NaCl, 1% Triton X-100, 1.5 mM $MgCl_2$, 1 mM EDTA, 1 mM DTT, and 1 mM PMSF/Protease inhibitors).

In Vitro RNA Pull-Down Assay

Peptide pull-down assay was performed by partially modified methods from the existing document (Heo and Sung, (2011) Science 331, 76-79). Synthetic biotinylated let-7a-1 (5'-Biotin-UGUAUAGUUUUAGGGUCACAC-CCACCACUGGGAGAUAACUAUACA-3') and miR-16-1 (5'-Biotin-GUAAAUAUUGGCGUUAAGAUUC-UAAAAUUAUCUCCAGUAUUAACU-3') RNAs were synthesized and purified using RNase Free HPLC of IDT (Integrated DNA technologies; Iowa, USA). Nuclear extracts were obtained from samples transformed with LIN28A and K135R, 10 μg biotinylated RNAs and 200 μg of nuclear extract were added to pull-down buffer (50 mM Tris pH 7.5, 150 mM NaCl, 2 mM DTT, 0.05% NP-40, 1 mM PMSF/Protease inhibitors) containing RNasin (Promega) added thereto, mixed with each other, and reacted at 4° C. for 6 hours. Each reactant was added to 30 ul of washed streptavidin-coated Dynabeads M280 (Invitrogen) and reacted at 4° C. for 1 hour more. The obtained products were washed three times with peptide pull-down buffer, separated by SDS-PAGE, and analyzed by immunoblot.

RNA Immunoprecipitation (RIP)

RIP assay was performed by partially modified methods from the existing document (Heo and Sung, (2011) Science 331, 76-79). Briefly, cells were washed twice with PBS, 1% formaldehyde (Sigma) was added at room temperature for 10 minutes to perform cross-linking, followed by quenching with 125 mM glycine. Cross-linked cells were recovered in PBS and cell-lysed with 400 ul RIPA buffer (50 mM Tris-Cl, pH 8.0, 150 mM NaCl, 0.05% SDS, 1 mM EDTA, 1% NP-40, 0.05% sodium deoxycholate) with RNasin (Promega), followed by sonication three times for each 5 seconds using Sonic Dismembrator (Model 500, Fisher) equipped with stepped microtip (Fisher). Then, the obtained products were treated with DNase I at 37° C. for 10 minutes, and centrifuged for 15 minutes at 4° C. and 13,000 rpm (Eppendorf). The obtained products were divided by 5%, and frozen at −80° C. Each sample was reacted with antibodies to be confirmed and RNasin at 4° C. for 2 hours for an immunoprecipitation experiment. In order to recover the resulting immune complexes, 40 ul of protein A and G-agarose (GE healthcare) were added to each tube, and reacted in a rotating stirrer for 2 hours or more. Then, immune complexes were washed once with Low Salt Wash Buffer (20 mM Tris-Cl, pH 8.0, 150 mM NaCl, 2 mM EDTA, 0.1% SDS and 1% Triton X-100), High Salt Wash Buffer (20 mM Tris-Cl, pH 8.0, 500 mM NaCl, 2 mM EDTA, 0.1% SDS, and 1% Triton X-100), LiCl buffer (10 mM Tris-Cl, pH 8.0, 250 mM LiCl, 1 mM EDTA, 0.5% NP-40, 0.5% Sodium deoxycholate), and twice with TE buffer (10 mM Tris-Cl, pH 7.5, 1 mM EDTA) for 10-15 minutes, respectively Immune complex was reacted by rotation stirring with 100 ul elution buffer (1% SDS, 0.1 M $NaHCO_3$) at 25° C. for 15 minutes to be repeatedly eluted. 16 ul of 5 M NaCl (200 mM) was added to 200 ul of eluent, and heated at 70° C. for 1 hour, for reverse cross-linking To remove DNA, immune complex was treated with DNase I for 10 minutes, and RNA was separated from the samples with TRIZOL™ Reagent (Invitrogen) in accordance with the manufacturer's instruction.

RNA Interference

Sequences capable of effectively inhibiting expression of LIN28A and SET7/9 were selected as follows. CTA-CAACTGTGGAGGTCTA (SEQ ID NO: 3), GCCTTG-TAGGAGAAGTAAA (SEQ ID NO: 4). siRNA for EGFP was selected as a control group. GTTCAGCGTGTCCGGC-GAG (SEQ ID NO: 5). siRNA duplex synthesized by 21 nucleotide sequences was produced by Samchully Pharm (Seoul, Korea). NCCIT cells (2×105 cells/well) were inoculated in 6-well plate, and after 24 hours, the cells were transformed with 100 nM LIN28A, SET7/9, or 60 nM control siRNA by DharmaFECT (Thermo) in accordance with the manufacturer's instructions. For embryonic stem cells, H9 cells were washed with PBS, and treated with Accutase (STEMCELL Technologies, Vancouver, Canada) in accordance with the existing document (Bajpai et al., (2008) MolReprod Dev 75, 818-827) at 37° C. for 5-10 minutes to separate cell colony into single cells. Then, the cells were centrifuged at 800 rpm for 5 minutes, and about $1\times10^5$ cells/ml was re-inoculated in matrigel (BD Biosciences, San Diego, Calif.), and cultured in condition medium containing 10 uM ROCK inhibitor (Y-27632; Sigma-Aldrich, USA) added thereto for 48 hours, wherein feeder cells are not inoculated. These single cells were cells transformed by siRNA as described above, and at 72 hours after transformation, the cells were analyzed by immunoprecipitation method or RT-qPCR method. A condition medium used for culture medium was obtained by culturing mct-MEFs with a concentration of $9.8\times10^6$ cells/T175 flask in embryonic stem cell culture medium under humid condition at 37° C. and 5% $CO_2$, for 7 days, to recover suspension every day, and filtering the suspension by 0.22 um filter (Corning Incorporated Life Sciences, MA) and freezing the filtrate.

Gene Expression Microarray Analysis

Total RNA was extracted with Trizol Reagent (Molecular Research Center, Cincinnati, Ohio, USA) in accordance with manufacturer's instructions and absorbance was measured at 260 nm for quantification, and purity was confirmed by Bioanalyzer 2100 (Agilent, Calif., USA). Agilent's Low RNA Input Linear Amplification kit (Agilent Technology; G4140-90040) was used to produce Cyanine 3-labeled cRNA (complementary RNA), and labeled cRNA was also quantified by nanodrop spectrophotometer. Then, Agilent SurePrint G3 Human Gene Expression 8×60K Microarray kit having 50,599 biologically specific materials and 1280 positive control materials was used for experiment, and microarray after hybrid reaction was washed with Agilent's Gene Expression Wash Buffer Kit. Each hybrid was used for each sample. Agilent's DNA microarray scanner (G2505B) was used to image microarray chip, and primitive signal strength was obtained by using Feature Extraction Software (Agilent Technology) and treated with Limma R package. Displacement standardization was performed, and gene having low signal intensity was removed, and duplicate probe representing the same gene was shown by an average value. Genes having expression level difference by three times or more or genes having significant expression level difference in LIN28A or SET7/9 knock-down and EGFP control group or in both were selected. Gene ontology analysis showing differential expression using GOEAST (http://omicslab.genetics.ac.cn/GOEAST/index.php) (Zheng and Wang, (2008) Nucleic Acids Res 36, W358-W363) was performed.

Example 1

Identification of Methylation Position of LIN28A

<1-1> Methylation Enzyme Analysis

In vitro pull-down assay was performed using 6×HIS-labeled human LIN28A expressed and purified in microorganisms, and methylation analysis was performed by using various HMTase (histone methyltransferases) expressed in microorganisms such as PRMT6, SET8, SET7/9, DOT1L, SMYD2, SMYD3, SMYD4, SMYD5-S, SMYD5-L, and the like.

As a result, as shown in FIG. 1, several HMTases were non-specifically bound to LIN28A; however, all HMTases except for SET7/9 did not show enzyme activity with respect to LIN28A. Accordingly, it was considered that LIN28A was methylated by lysine methylation.

<1-2> Immunoprecipitation Analysis

In order to confirm whether LIN28A is bound to SET7/9, physical binding capacity of LIN28A and SET7/9 was measured by in vivo immunoprecipitation analysis.

As a result obtained by performing immunoprecipitation on endogenous LIN28A and over-expressed LIN28A, followed by immunoblot analysis using antibodies, SET7/9 was detected in H9, NCCIT and HEK293T cells, respectively, to demonstrate that LIN28A was physically bound with SET7/9 in the body ([FIG. 2A], [FIG. 2B] and [FIG. 3A]). LIN28A was not reacted in a negative control group that reacts with IgG, and conversely, even when immunoprecipitation was performed on SET7/9, the same results were shown ([FIG. 3A] to [FIG. 3C]).

<1-3> Search of Methylation Expected Location

Next, positions in which LIN28A was methylated by SET7/9 were accurately measured. Amino acid sequences of LIN28A were compared with sequences around SET7/9 methylation target site having histone H3 (Nishioka et al., (2002) Genes Dev 16, 479-489; Wang et al., (2001) Nature 444, 364-368), p53 (Chuikov et al., (2004) Nature 432, 353-36), TAF10 (Kouskouti et al., (2004) Mol Cell 14, 175-182), DNMT1 (Esteve et al., (2009) Proc Natl AcadSci U.S.A 106, 5076-5081), ERa (Subramanian et al., (2008) Mol Cell 30, 336-347), and E2F1 (Kontaki and Talianidis, (2010) Mol Cell 39, 152-160).

As a result, as shown in [FIG. 2C], lysine 135 of a linker region that meets RNA bonding domain of LIN28A and surrounding residues thereof were preserved to be almost similar to K/R-S/T-K (Couture et al., (2006) Nat StructMolBiol 13, 140-146) which was SET7/9 recognition sequence. FIG. 2C shows sequence comparison results for the protein sequences that are identified in Table 2 below with their corresponding SEQ ID NOS.

TABLE 2

| Protein Identification | SEQ ID NO: | Amino Acid Sequence |
|---|---|---|
| Histone H3 (1-11) | SEQ ID NO: 55 | ARTKQTARKST |
| p53 (365-379) | SEQ ID NO: 56 | HSSHLKSKKGQSTSR |
| TAF10 (182-196) | SEQ ID NO: 57 | GSSRSKSKDRKYTLT |
| DNMT1 (135-149) | SEQ ID NO: 58 | PRTPRRSKSDGEAKR |
| ERa (295-309) | SEQ ID NO: 59 | PLMIKRSKKNSLALS |
| E2F1 (178-192) | SEQ ID NO: 60 | QLIAKKSKNHIQWLG |
| LIN28A (128-142) | SEQ ID NO: 61 | SMQKRRSKGDRCYNC |
| LIN28B (118-132) | SEQ ID NO: 62 | TLQKRKPKGDRCYNC |

Surprisingly, it could be appreciated that LIN28B homologous to LIN28A did not have SET7/9 recognition sequence, and even in results obtained by comparing total amino acid sequences of fly lin-28, larva lin-28, and LIN28A/B of humans, mice, frogs, SET7/9 recognition sequence of LIN28A sequence was obtained in an evolution process of higher eukaryotes such as *M. musculus* ([FIG. 3D]).

<1-4> Confirmation of Methylation Positions by Antigen-Antibody Reaction

For research into methylation activity by SET7/9 of LIN28A in vivo, multivalent antibodies specific to non-methylated LIN28A-K135 and to LIN28A-K135 with one methyl group attached thereto were produced. The produced multivalent antibodies were tested with respect to LIN28A peptide with one methyl group at K135 or non-modified LIN28A peptide, and antibody that specifically detects only one of one methylated peptide or non-modified LIN28A was selected [FIG. 2D].

In order to confirm whether lysine 135 of LIN28A was methylated by SET7/9 in vivo, FLAG-labeled LIN28A wild type or FLAG-LIN28A-K135R (K135R; mutants in which lysine 135 which is a recognition site of SET7/9 in LIN28A was substituted with arginine) was transfected in HEK293T cell.

As a result of immunoblot analysis using anti-LIN28A-K135-me1 antibody that recognizes the methylated LIN28A, as shown in [FIG. 2E], the antibody reacted with over-expressed LIN28A wild type; however, did not recognize K135R. Accordingly, it could be appreciated that lysine 135 of LIN28A was methylated in vivo, and in particular, LIN28A transfected in HEK293T cell was methylated by SET7/9 in the cell.

Example 2

Identification of Binding Characteristic of SET7/9 and LIN28A

<2-1> Test of Direct Bonding of SET7/9

In order to confirm that whether LIN28A and SET7/9 directly react in vivo, MAL, 6×HIS, GST fusion proteins sequentially fused with full length of LIN28A and SET7/9 were produced and confirmed ([FIG. 4C] and [FIG. 4D]). The produced fusion proteins were subjected to GST pull-down analysis.

Figure 5:
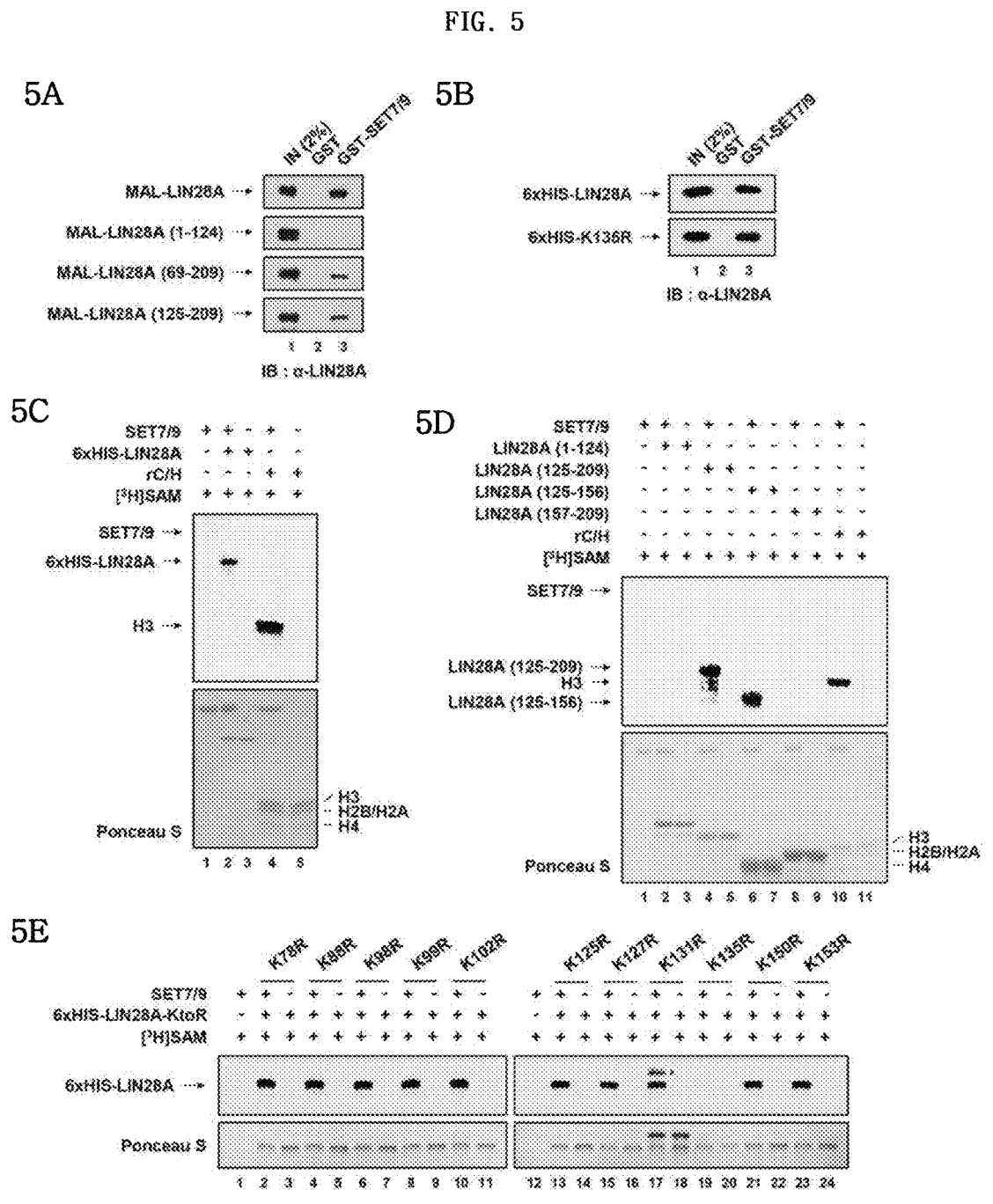

As a result, it was confirmed that carboxyl terminus of LIN28A (amino acids 125-209) reacted with the SET7/9 ([FIG. 5A], [FIG. 4A] and [FIG. 4B]). Surprisingly, all of normal LIN28A and K135R mutant were bound to SET7/9 ([FIG. 5B]). From the above results, direct reaction between LIN28A and SET7/9 was confirmed.

<2-2> Methylation Experiments of LIN28A by SET7/9

Next, it was confirmed whether LIN28A was methylated by SET7/9 in vitro. It was confirmed whether full-length recombinant LIN28A reacted with recombinant SET7/9 in $^3$H—S-adenosine-methionine ([$^3$H] SAM), and recombinant LIN28A was methylated (FIG. 5C], lane 2). When there was no SET7/9 protein, it was confirmed that LIN28A was not methylated ([FIG. 5C], lane 3), and LIN28A was methylated by SET7/9 in vitro. Recombinant human histone core (rC/H) as a positive control group was methylated by SET7/9 under the same conditions as LIN28A, and it was demonstrated by in vitro-methyl transferase assay ([FIG. 5C], lane 4, 5, [FIG. 4E]).

<2-3> Confirmation of Methylation Positions by Methyl Transferase Assay

It was confirmed that the full length LIN28A was methylated in vivo and in vitro by SET7/9, such that an experiment for confirming that potential methylation position, lysine 135, is an actual target position of SET7/9 was conducted. 6×HIS-labeled proteins including 4 different fragments of LIN28A were expressed in bacteria and purified therefrom, and these proteins were subjected to in vitro methyl transferase assay.

As a result, it was confirmed that only LIN28A (125-209) and (125-156) having lysine 135 among 4 fragments were methylated by SET7/9 ([FIG. 5D], lane 4, 6), and LIN28A (1-124) and (157-209) without lysine 135 were not methylated ([FIG. 5D], lane 2, 8).

<2-4> Mutation Substitution Test of Site at which Methylation is Possible

There are several lysines around Lysine 135. As an experimental result obtained by substituting total of 11 lysines of K78, K88, K98, K99, K102, K125, K127, K131, K150, and K153 including K135 with arginines so as not to be methylated, a methylation reaction by SET7/9 was completely removed in K135 mutant ([FIG. 5E], lane 19), which clearly showed that lysine 135 of LIN28A is methylated by SET7/9.

<2-2> Experiment of LIN28-Specific Methylation Characteristic of SET7/9

As shown in [FIG. 2C], LIN28B does not have a target position of SET7/9 of LIN28A. Accordingly in order to confirm that specific methylation was generated in K135 of LIN28A, LIN28B was expressed in bacteria, and in vitro methyl transferase analysis was performed. As expected, LIN28B was not methylated by SET7/9 ([FIG. 6A]). As a negative control group, DOT1L known as H3 K79 methyl transferase was expressed and purified by baculovirus expression system (Kim et al., (2013) J BiolChem 287, 39698-39709), and methyl transferase assay was performed under the same conditions. As a result, it was confirmed that LIN28A was not methylated ([FIG. 6B]). To sum it up, it could be appreciated that LIN28A at K135 was specifically single-methylated by SET7/9.

Example 3

Experiment of Increase in Stability of LIN28A by Methylation

<3-1> Measurement of Intracellular Level of LIN28A Protein

Figure 7:
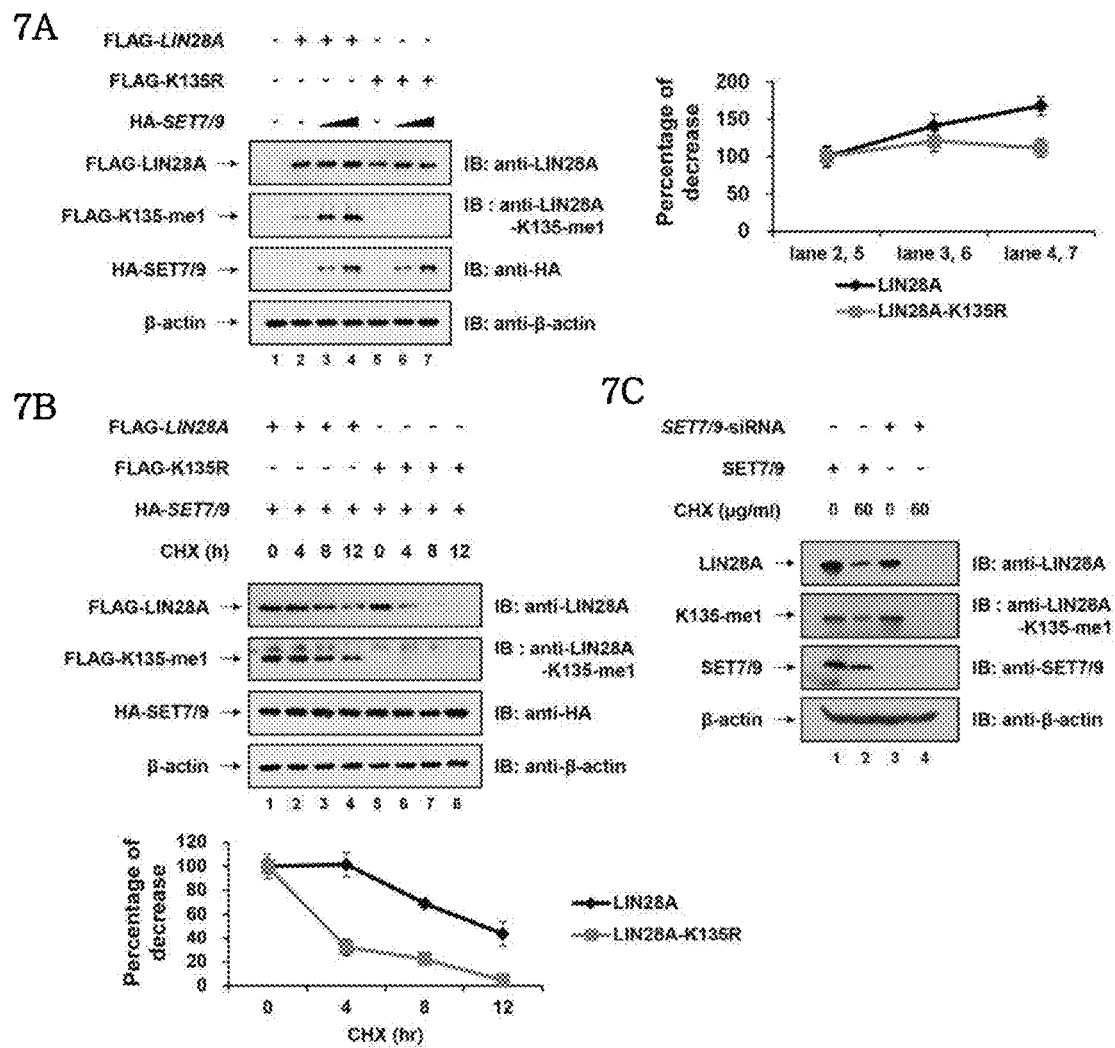
FIG. 7 shows experimental results showing an increase in stability of LIN28A due to lysine methylation by SET7/9.

It has reported that methylation of lysine by SET7/9 serves to control stabilization of p53 (Chuikov et al., (2004) Nature 432, 353-360), TAF10 (Kouskouti et al., (2004) Mol Cell 14, 175-182), DNMT1 (Estve et al., (2009) Proc Natl AcadSci U.S.A 106, 5076-5081), ERa (Subramanian et al., (2008) Mol Cell 30, 336-347), and E2F1 (Kontaki and Talianidis, (2010) Mol Cell 39, 152-160) which are target proteins having R/K-S/T-K sequence. Accordingly, whether methylation by SET7/9 affects stabilization of in vivo LIN28A was examined. As a result obtained by co-expressing SET7/9 in HEK293T cells increasing expression of LIN28A in which K135R was not expressed [(FIG. 7A]), LIN28A methylated by SET7/9 had increased stability.

<3-1> Measurement of Intracellular Half-Life of LIN28A Protein

To further support this, it was confirmed that level of LIN28A mRNA was not changed in the cells in which SET7/9 was co-expressed ([FIG. 8A], [FIG. 8B]). In order to confirm that the stabilization of the protein is caused by the methylation generated in lysine 135 of LIN28A, an experiment to figure out effects of SET7/9 for the half-life of normal LIN28A and LIN28A-K135R was conducted.

As a result, as the same results as previously confirmed, LIN28A was defined by methylation, and the half-life of LIN28A-K135R was reduced ([FIG. 7B], [FIG. 8C]), but LIN28A was methylated by SET7/9 to be much more stable and the half-life thereof was significantly increased ([below FIG. 7B]). In addition, H9 or NCCIT cell in which SET7/9 was reduced by transfection of siRNA also showed stability of LIN28A ([FIG. 7C], [FIG. 8D]). These results demonstrate that lysine 135 of LIN28A was methylated to provide increase in stability of LIN28A.

Example 4

Identification of Characteristic of Methylated LIN28A

<4-1> Measurement of Intracellular Distribution of Methylated LIN28A Protein

LIN28A and LIN28B are present differently in cells. LIN28A is found mainly in cytoplasm from the nematode to the mammal, and rarely found in the nucleus. Meanwhile, the most of LIN28B is present in nucleus, in particular, nucleolus, due to its functional NLS (nuclear localization signals) and NoLS (nucleolar localization signals), to block processing of pri-let-7 miRNAs by microprocessor. Meanwhile, LIN28A inhibits a Dicer step in the cytoplasm, and induces oligo-uridylation of pri-let-7 by Tut4 (Zcchc11).

In particular, K135 which is a position of LIN28A methylation and surrounding sequences thereof have homology with NoLS of LIN28B ([FIG. 4A] and [FIG. 10D]). In addition, LIN28A and LIN28B are present in cells in the manner of mutual exclusion. In order to examine intracellular distribution of the methylated form of LIN28A, K135R which is LIN28A over-expressed in nucleus and cytoplasm in HEK293T, H9 and NCCIT cell lines and endogenous LIN28A were subjected to biochemical fraction and immunoblot with antibodies was performed ([FIG. 9A], [FIG. 9B], and [FIG. 10B]).

As the same as open source, LIN28A in all cells was abundant in the cytoplasm and scarce in the nucleus. Meanwhile, the methylated form of LIN28A was present in the nucleus. Interestingly, it was confirmed that the methylated form of LIN28A was present in phosphorus (nucleolus) as well as nucleoplasm in H9 cell lines ([FIG. 9C]).

As immunofluorescence analysis results targeting H9, NCCIT, and HEK293T cell lines, it was found that large amounts of single-methylated LIN28A and SET7/9 were found in nucleus, in particular, in phosphorus (nucleolus) together with fibrillarin which is a marker of phosphorus ([FIG. 9D], [FIG. 10A], and [FIG. 10C]).

In order to further demonstrate that the single-methylated LIN28A was present in the nucleus by SET7/9-mediated methylation, as a knock down result of SET7/9 using siRNA, it was confirmed that patterns in which nuclear form LIN28A was specifically present in nucleus were reduced, by immunoblot and immunofluorescence analysis ([FIG. 9E]).

From these results, it was determined that single methylated LIN28A by SET7/9 at K135 serves as NoLS of LIN28B in the nucleus. Sequence analysis of analogs of LIN28B supports this fact ([FIG. 10D]).

Different intracellular distributions of non-methylated form (hereinafter referred to as cytoplasm type) and single-methylated form (referred to in nuclear form) LIN28A suggests that LIN28A modified by lysine methylation isolates transcriptome of primary let-7 (pri-let-7) miRNA in nucleolus by Tut4 (Zcchc11) independent method, like LIN28B, to inhibit biosynthesis thereof.

Example 5

Inhibition of Biosynthesis of -Pri-Let-7 Identifying Characteristic of Single Methylated LIN28A <5-1> miRNA Processing Inhibition Test of Single Methylated LIN28A Protein Single-methylated position of LIN28A is a position corresponding to NoLS of LIN28B and the single methylated LIN28A is accumulated in the nucleus, and accordingly, LIN28A may remain in the nucleus by methylation of K135 in embryonic stem cells and human cells. As compared to LIN28B (Piskounova et al., (2011) Cell 147, 1066-1079), methylation at K135 of LIN28A is a signal generated only in the nucleus, and increases stability of LIN28A ([FIG. 7], [FIG. 8], [FIG. 9], [FIG. 10]). From the results, a hypothesis that LIN28A was single-methylated in the nucleus to inhibit processing of the pri-let-7-1 miRNA by Tut4 (Zcchc11) independent manner, was made.

In order to confirm that the nuclear form of LIN28A inhibits miRNA processing, the pri-let-7a-1 and luciferase genes having three let-7a binding sites together with FLAG-labeled normal LIN28A that is capable of being methylated and FLAG-labeled LIN28A-K135R that is not capable of being methylated were configured so as to be target of mature let-7a-1, and transfected in HEK293T cell and quantitative RT-PCR (RT-qPCR) was performed ([FIG. 11A]). In cells simultaneously transfected with normal FLAG-LIN28A or FLAG-K135R and pri-let-7a-1 and let-7aBS-Luc, pri-let-7a-1 RNA and luciferase mRNA were allowed to be accumulated as the same as the reduction of mature let-7a-1 RNA. In particular, an amount of pri-let-7a-1 RNA accumulated by methylated LIN28A was remarkably larger than that of non-methylated LIN28A ([FIG. 11A], lane 4, 5), which corresponds to the fact that these proteins were present in the nucleus at a different ratio as shown in [FIG. 9A]. However, it appears that mature let-7 miRNA was also significantly reduced by the non-methylated LIN28A ([FIG. 11A], lane 5, [FIG. 12C], lane 4), which is caused by LIN28B that is potentially capable of processing mature let-7 miRNA. As positive control groups, it was observed that Luciferase mRNA was reduced up to twice due to RISC (RNA-induced silencing complex), AGO2 repressing miRNA-mediated translation (Lytle et al., (2007) Proc Natl AcadSci USA 104, 9667-9672) active ingredient ([FIG. 11A], lane 6).

Interestingly, FLAG-LIN28A over-expressed in HEK293T cells was significantly methylated by SET7/9 in the cells ([FIG. 12A], lane 4, [FIG. 12B], lane 4), which shows that LIN28A interfering pri-let-7 miRNA processing in the nucleus as previously reported is a single methylated LIN28A in HEK293T cells (Heo et al., (2008) Mol Cell 32, 276-284; Viswanathan et al., (2008) Science 320, 97-100). In the similar results of using pri-let-7g which is another let-7 type ([FIG. 12C], [FIG. 12D]), it shows that LIN28A nuclear form specifically targets let-7 type, unlike miR-16-1 ([FIG. 11B]) which is a negative control group.

<5-2> Measurement of Let-7 miRNA Expression Level by LIN28A

In order to confirm that LIN28A nuclear form is possible to perform processing of mature let-7 miRNA into cells, expression levels of all let-7 type components were measured in HET293T cell expressing the same amount of proteins by transfection with FLAG-LIN28A or FLAG-K135R through RT-qPCR ([FIG. 12E]). Pri-let-7 type components in all measured cells were significantly increased by over-expressed LIN28A than K135R; meanwhile, level of mature miR-16 and miR-21 in the cells was not affected ([FIG. 12F], above). It was observed that pri-let-7 was accumulated to a level corresponding to the reduction of mature let-7 type components by LIN28A capable of being methylated ([FIG. 12F], below). Next, in order to confirm that LIN28A nucleus form is an inhibitor in the cell inhibiting biosynthesis of miRNA in embryonic stem cells, LIN28A or SET7/9 was subjected to knock-down in H9 human embryonic stem cells using siRNA targeting LIN28A or SET7/9 ([FIG. 11C]). When LIN28A was knocked down, the half-life of the mature miRNA was increased to accumulate mature let-7 components in H9 cell (Kim, 2005); however, miRNA level of other negative control group was not changed ([FIG. 11C], below). When LIN28A was knocked down, level of primary let-7 was also reduced corresponding to accumulation level of mature let-7 type components ([FIG. 11C], above) Even in a case in which SET7/9 was knocked down to reduce methylation of LIN28A, mature let-7 was increased ([FIG. 11C], S7F, green) to obtain results similar to the previous results. To sum it up, it shows that LIN28A nuclear form which is single-methylated and activated in the nucleus, completely inhibits the processing of the pri-let-7.

Example 6

Experiment of Intranuclear Reaction Mechanism of LIN28A

<6-1> Comparison of Relative Binding Capacity of LIN28A with Respect to Pri-Let-7 RNA In order to explain the inhibition process of let-7 processing induced by the single methylated LIN28A in detail, relative binding abilities of intracytoplasmic LIN28A and intranuclear LIN28A with respect to pri-let-7 RNA were compared to each other. RNA-binding in vitro was analyzed by using nuclear extracts of HEK293T cells transfected with FLAG-LIN28A or FLAG-K135R together with synthesized biotinyl let-7a-1 RNA having loop at the terminal ([FIG. 13A]). As the same as the fact in which LIN28A was selectively bound to stem-loop portion of the pre-let-7 miRNA (Piskounova et al., (2008) J BiolChem 283, 21310-21314), it was found that an amount of let-7a-1 RNA bound to intranuclear LIN28A was remarkably larger than that of intracytoplasmic LIN28A ([FIG. 13A], lane 5). Meanwhile, both forms of LIN28A were not bound to mir-16-1 miRNA ([FIG. 13A], lane 7), and SET7/9 used as a negative control group was not bound to both of let-7a-1 and mir-16-1 RNA.

In order to further analyze in more detail whether intranuclear LIN28A was bound to the pri-let-7 so as to interfere with the processing, RNA bound to intranuclear LIN28A in vivo was examined. FLAG-LIN28A or FLAG-K135R were expressed, respectively, RNA immunoprecipitation (RIP) analysis was performed by IgG, LIN28A (antibody capable of detecting both of methylated LIN28A and unmethylated LIN28A), and each body with respect to LIN28A-K135-me1 or LIN28A-K135-me0, and relative levels of pri-let-7a-1 was analyzed by RT-qPCR. Analysis results showed that intranuclear LIN28A was directly bonded to the pri-let-7a-1 in the nucleus as compared to intracytoplasmic LIN28A ([FIG. 13B], the left side). Amounts of the pri-let-7a-1 bound to intranuclear LIN28A detection were detected with anti-LIN28A LIN28A-K135-me1 antibodies, respectively, and were higher by 2.8 times and 6.6 times, respectively. Increases of LIN28A-K135-me0 signal between the two cases were not significantly different, which means that the main form of the methylated LIN28A is bound to pre-let-7a-1 in the nucleus. In addition, it was found that the LIN28A mRNAs were bound to LIN28A capable of being methylated in a significantly larger amount than that of LIN28A capable of not being methylated in the nucleus (K135R mutant); meanwhile, LIN28A capable of not being methylated in the nucleus (K135R mutant) was bound to LIN28A mRNA (FIG. 13B], right side), and LIN28A-K135-me0 signals in both of two cases were not significantly different. This result corresponds to the description (Wilbert et al., (2012) Mol Cell 48, 195-206) in which LIN28A performs self-controlling to be increased by binding LIN28A to 3'UTR of mRNA itself. Slow increase of LIN28A mRNA bound to intracytoplasmic LIN28A immunoprecipitated with anti-me 1 antibody is because the number of intracytoplasmic LIN28As is excessively increased in the cytoplasm, such that antibodies thereof are non-specifically bound. To sum the results from [FIG. 7] to [FIG. 11], LIN28A capable of being methylated and stabilized in the nucleus preferentially reacts with pri-let-7a-1, which is regarded that the intranuclear LIN28A affects potential mechanism directly involved in controlling the processing of the pri-let-7 miRNA.

<6-2> Search of SET7/9 Binding Motif of LIN28A

LIN28A will be primarily bound to 3'UTR of mRNAs itself through several important LIN28A binding motifs on the basis of GGAGA sequence (Cho et al., (2012) Cell 151, 765-777; Wilbert et al., (2012) Mol Cell 48, 195-206). Surprisingly, LIN28A is bound to SET7/9 mRNA as well as mRNA itself ([FIG. 14A]). Accordingly, in order to confirm that SET7/9 has LIN28A biding motif, the present inventors examined more motifs at LIN28A 3'UTR ([FIG. 14B]). These results suggest that LIN28A is bound to 3'UTR of SET7/9 to control translation of SET7/9 mRNA. In order to demonstrate this fact, FLAG-LIN28A or FLAG-K135R was transfected into HET293T cell, and the expression of SET7/9 was confirmed. In particular, both of intranuclear LIN28A and intracytoplasmic LIN28A affects the translation rather than transcription of SET7/9 ([FIG. 14C], [FIG. 14D]). Surprisingly, LIN28A capable of being methylated significantly increases the translation of the SET7/9 mRNA as compared to LIN28A capable of not being methylated. It suggests that LIN28A has a significant influence on mRNA processing of forming mRNP capable of discharging the intranuclear LIN28A to the outside of the nucleus, or on stabilization of SET7/9 mRNA in the nucleus. In summary, it is considered that LIN28A is bound to the 3'UTR of SET7/9 to increase the translation. Eventually, LIN28A may affect in making RNA secondary structure by reconstructing mRNP like chaperone, and may be involved in a control process after transcription of a number of genes (Hafner et al., (2013) RNA 19, 613-626; Semrad, (2010) Biochem Res Int 2011).

Example 7

Cell Potency-Related Gene Regulation Experiment of LIN28A

The nuclear form LIN28A methylated by SET7/9 controls cell potency and differentiation potency of the stem cells by specifically regulating let-7 miRNA.

<7-1> Measurement of Change of LIN28A and SET7/9 by N28A or SET7/9 Knock-Down

Primary transcriptomes of Let-7 miRNA may be easily detected in undifferentiated embryonic stem cells. However, mature let-7 miRNA is not detected in embryonic stem cells, but is significantly highly induced in a differentiation process after transcription (Thomson et al., (2006) Genes Dev 20, 2202-2207, Viswanathan et al., (2008) Science 320, 97-100). In [FIG. 11C], and the like, as mature let-7 components are increased in embryonic stem cells, level of pri-let-7 is decreased as corresponding thereto (Viswanathan et al., (2008) Science 320, 97-10).

Accordingly, importance of LIN28A and single-methylated LIN28A by SET7/9 in controlling cell potency of embryonic stem cells by a method of controlling let-7 miRNA which play an important role in the differentiation process in H9 cell and NCCIT cell was evaluated.

Figure 15:
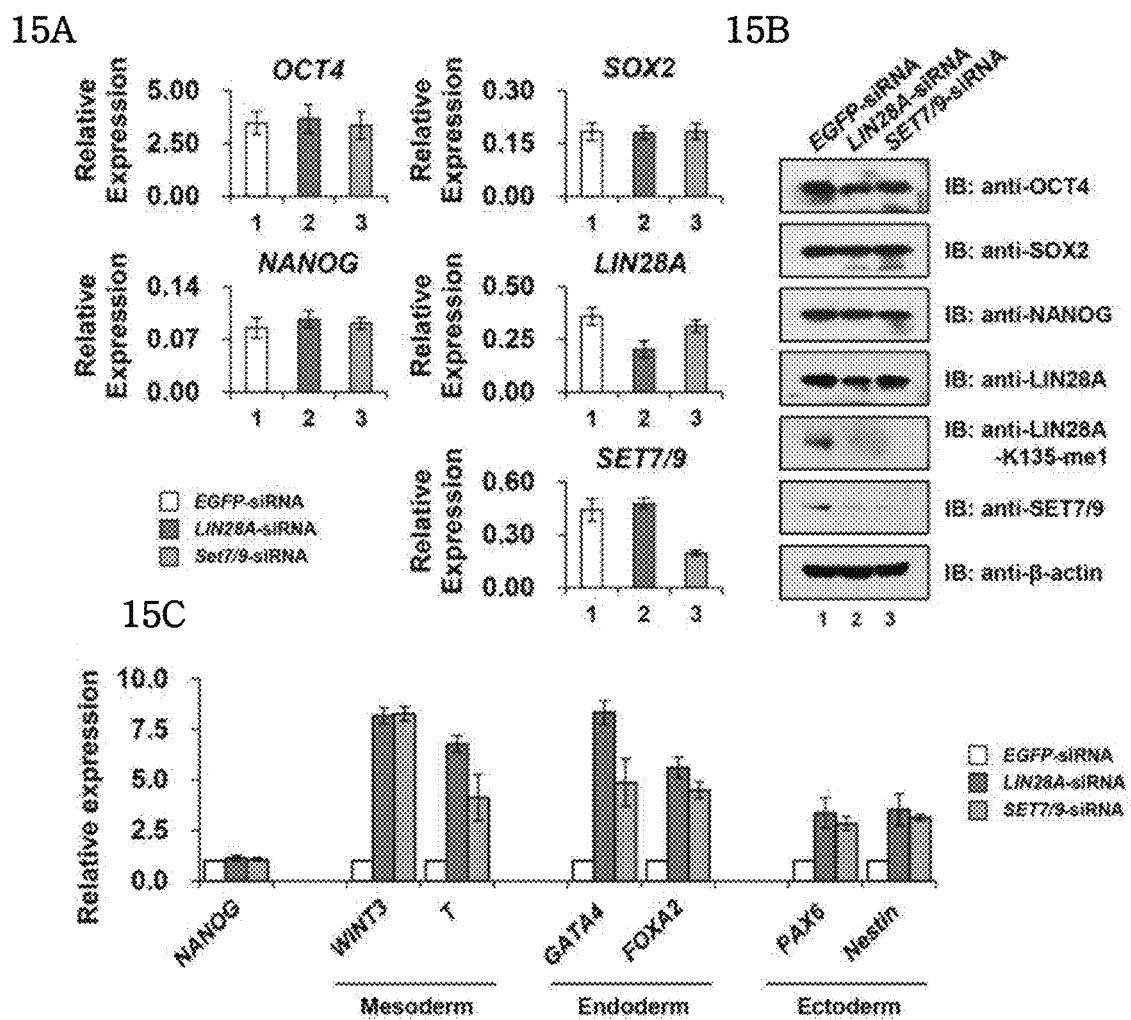
FIG. 15 shows experimental results confirming that LIN28A and SET7/9 are involved in polymorphism regulation in H9 cell line.

As a result, after transfection with N28A-siRNA or SET7/9-siRNA, protein expression of LIN28A or SET7/9 and level of mRNA were decreased, respectively ([FIG. 15A], [FIG. 15B], [FIG. 16A], [FIG. 16B]). Surprisingly, unlike cells transformed with EGFP-siRNA used as a control group, LIN28A knock-down did not affect expression of representative cell potency regulatory genes such as NANOG and SOX2, and exceptionally, OCT4 is controlled in the process after transcription by LIN28A (Qiu et al., (2010) Nucleic Acids Res 38, 1240-1248). In particular, when LIN28A was knocked down, SET7/9 mRNA was significantly reduced (FIG. 15B], lane 2, [FIG. 16B], lane 3), which supports results that LIN28A increases translation of SET7/9.

<7-2> Transcription Expression Profiling Experiment

In order to further find out role of the methylation of LIN28A in controlling cell potency, transcription expression profiling of H9 cells in which LIN28A or SET7/9 was reduced was performed. On the basis of genes showing expressions changed by three times or more, genes showing significant increase or decrease were selected. Distribution of genes showing significant change on the basis of the reference value was evaluated by MA plot ([FIG. 17A]). Among them, as compared to EGFP control group, 555 (320 increased, 235 decreased) genes showing expression change in LIN28A knockdown cell and 644 (385 increased, 259 decreased) genes showing expression change in SET7/9 knock-down cell were confirmed, respectively. Significantly high positive correlation (r=0.86~0.88) was shown between the genes showing expression change in LIN28A knockdown cell and the genes showing expression change in SET7/9 knock-down cell ([FIG. 17B]), which means that LIN28A and SET7/9 have common function. The genes showing expression changes were significantly involved in developmental processes ([FIG. 17C], [FIGS. 18A-C]). In order to further support these results, expression level of the early lineage markers was measured. In particular, increase in expression of the representative early lineage markers was observed the LIN28A or SET7/9 was knocked down ([FIG. 17D]). In order to verify the reliability of the expression of the genes obtained by microarray analysis, comparative RT-qPCR was performed ([FIG. 15C], [FIG. 16C]).

In cells in which LIN28A was knocked down, unexpectedly weak induction of the early lineage markers is because the expression levels of cell potency regulatory genes are not largely changed, which shows that the lineage markers are increased by let-7 in the initial differentiation step. Therefore, the induction of mature let-7 is caused by direct effect of intracytoplasmic LIN28A affecting pre-let7 miRNA biosynthesis and intranuclear LIN28A affecting pri-let7 biosynthesis, rather than by indirect differentiation by other factors. Several target genes of Let-7 miRNA begin to affect from early differentiation stage ([FIG. 18D]). In summarizing all results, LIN28A and SET7/9 have an important function in controlling cell potency and differentiation potency by specifically controlling let-7 miRNA.

The present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

INDUSTRIAL APPLICABILITY

The method of the present invention is possible to screen materials capable of controlling pluripotency of embryonic stem cells or materials having anti-cancer activity, and the materials screened by the method of the present invention may control pluripotency of embryonic stem cells and inhibit growth of cancer cells, which is effective for disorders of stem cell differentiation or preparation of cancer therapeutic agent to provide high industrial applicability.

The invention claimed is:

1. A method for treating cancer, comprising: treating with a composition including an inhibitor of methylation of 135th lysine of LIN28A by binding between LIN28A and SET7/9; wherein the inhibitor is siRNA consisting of the sequence of SEQ ID NO: 4 as a sense strand and complementary sequence thereof as an antisense strand.

* * * * *

UNITED STATES PATENT AND TRADEMARK OFFICE
CERTIFICATE OF CORRECTION

PATENT NO. : 9,650,633 B2  
APPLICATION NO. : 14/778600  
DATED : May 16, 2017  
INVENTOR(S) : Daeyoup Lee et al.

Page 1 of 1

It is certified that error appears in the above-identified patent and that said Letters Patent is hereby corrected as shown below:

In the Claims

Column 3, Line 61: "mPRMT6, MAL-SETS, MAL-SET7/9" should be -- mPRMT6, MAL-SET8, MAL-SET7/9 --.

Column 21, Line 63: "PRMT6, SETS, SET7/9, DOT1L" should be -- PRMT6, SET8, SET7/9, DOT1L --.

Signed and Sealed this  
Twentieth Day of June, 2017

Joseph Matal  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 62

<210> SEQ ID NO 1
<211> LENGTH: 45
<212> TYPE: RNA
<213> ORGANISM: Artificial Sequence
<220> FEATURE:
<223> OTHER INFORMATION: let-7a-1

<400> SEQUENCE: 1
uguauaguuu uagggucaca cccaccacug ggagauaacu auaca            45

<210> SEQ ID NO 2
<211> LENGTH: 45
<212> TYPE: RNA
<213> ORGANISM: Artificial Sequence
<220> FEATURE:
<223> OTHER INFORMATION: miR-16-1

<400> SEQUENCE: 2
guaaauauug gcguuaagau ucuaaaauua ucuccaguau uaacu            45
```

<210> SEQ ID NO 3
<211> LENGTH: 19
<212> TYPE: RNA
<213> ORGANISM: Artificial Sequence
<220> FEATURE:
<223> OTHER INFORMATION: sequence for siRNA of LIN28A

<400> SEQUENCE: 3
cuacaacugu ggaggucua                                                  19

<210> SEQ ID NO 4
<211> LENGTH: 19
<212> TYPE: RNA
<213> ORGANISM: Artificial Sequence
<220> FEATURE:
<223> OTHER INFORMATION: sequence for siRNA of SET7/9

<400> SEQUENCE: 4
gccuuguagg agaaguaaa                                                  19

<210> SEQ ID NO 5
<211> LENGTH: 19
<212> TYPE: RNA
<213> ORGANISM: Artificial Sequence
<220> FEATURE:
<223> OTHER INFORMATION: sequence for siRNA of EGFP

<400> SEQUENCE: 5
guucagcgug uccggcgag                                                  19

<210> SEQ ID NO 6
<211> LENGTH: 22
<212> TYPE: DNA
<213> ORGANISM: Artificial Sequence
<220> FEATURE:
<223> OTHER INFORMATION: LIN28A-RT-F

<400> SEQUENCE: 6
agcatgcaga agcgcagatc aa                                              22

<210> SEQ ID NO 7
<211> LENGTH: 22
<212> TYPE: DNA
<213> ORGANISM: Artificial Sequence
<220> FEATURE:
<223> OTHER INFORMATION: LIN28A-RT-R

<400> SEQUENCE: 7
gctaccatat ggctgatgct ct                                              22

<210> SEQ ID NO 8
<211> LENGTH: 22
<212> TYPE: DNA
<213> ORGANISM: Artificial Sequence
<220> FEATURE:
<223> OTHER INFORMATION: SET7/9-RT-F

<400> SEQUENCE: 8
tcattgatgt gcctgagccc ta                                              22

<210> SEQ ID NO 9
<211> LENGTH: 20
<212> TYPE: DNA
<213> ORGANISM: Artificial Sequence
<220> FEATURE:

<223> OTHER INFORMATION: SET7/9-RT-R

<400> SEQUENCE: 9
tcagggtgcg gatgcatttg						20

<210> SEQ ID NO 10
<211> LENGTH: 22
<212> TYPE: DNA
<213> ORGANISM: Artificial Sequence
<220> FEATURE:
<223> OTHER INFORMATION: OCT4-RT-F

<400> SEQUENCE: 10
aaacccacac tgcagcagat ca					22

<210> SEQ ID NO 11
<211> LENGTH: 22
<212> TYPE: DNA
<213> ORGANISM: Artificial Sequence
<220> FEATURE:
<223> OTHER INFORMATION: OCT4-RT-R

<400> SEQUENCE: 11
tcgttgtgca tagtcgctgc tt					22

<210> SEQ ID NO 12
<211> LENGTH: 23
<212> TYPE: DNA
<213> ORGANISM: Artificial Sequence
<220> FEATURE:
<223> OTHER INFORMATION: SOX2-RT-F

<400> SEQUENCE: 12
tgtggttacc tcttcctccc act					23

<210> SEQ ID NO 13
<211> LENGTH: 22
<212> TYPE: DNA
<213> ORGANISM: Artificial Sequence
<220> FEATURE:
<223> OTHER INFORMATION: SOX2-RT-R

<400> SEQUENCE: 13
tggtagtgct gggacatgtg aa					22

<210> SEQ ID NO 14
<211> LENGTH: 22
<212> TYPE: DNA
<213> ORGANISM: Artificial Sequence
<220> FEATURE:
<223> OTHER INFORMATION: NANOG-RT-F

<400> SEQUENCE: 14
accttccaat gtggagcaac ca					22

<210> SEQ ID NO 15
<211> LENGTH: 22
<212> TYPE: DNA
<213> ORGANISM: Artificial Sequence
<220> FEATURE:
<223> OTHER INFORMATION: NANOG-RT-R

<400> SEQUENCE: 15
tgcatgcagg actgcagaga tt					22

```
<210> SEQ ID NO 16
<211> LENGTH: 24
<212> TYPE: DNA
<213> ORGANISM: Artificial Sequence
<220> FEATURE:
<223> OTHER INFORMATION: GAPDH-RT-F

<400> SEQUENCE: 16
acatcaagaa ggtggtgaag cagg                                          24

<210> SEQ ID NO 17
<211> LENGTH: 22
<212> TYPE: DNA
<213> ORGANISM: Artificial Sequence
<220> FEATURE:
<223> OTHER INFORMATION: GAPDH-RT-R

<400> SEQUENCE: 17
caccctgttg ctgtagccaa at                                            22

<210> SEQ ID NO 18
<211> LENGTH: 21
<212> TYPE: DNA
<213> ORGANISM: Artificial Sequence
<220> FEATURE:
<223> OTHER INFORMATION: Firefly-RT-F

<400> SEQUENCE: 18
cgaaggttgt ggatctggat a                                             21

<210> SEQ ID NO 19
<211> LENGTH: 21
<212> TYPE: DNA
<213> ORGANISM: Artificial Sequence
<220> FEATURE:
<223> OTHER INFORMATION: Firefly-RT-R

<400> SEQUENCE: 19
cgcttccgga ttgtttacat a                                             21

<210> SEQ ID NO 20
<211> LENGTH: 21
<212> TYPE: DNA
<213> ORGANISM: Artificial Sequence
<220> FEATURE:
<223> OTHER INFORMATION: Renilla-RT-F

<400> SEQUENCE: 20
ttatcatggc ctcgtgaaat c                                             21

<210> SEQ ID NO 21
<211> LENGTH: 21
<212> TYPE: DNA
<213> ORGANISM: Artificial Sequence
<220> FEATURE:
<223> OTHER INFORMATION: Renilla-RT-R

<400> SEQUENCE: 21
ctgggtccga ttcaataaac a                                             21

<210> SEQ ID NO 22
<211> LENGTH: 21
<212> TYPE: DNA
<213> ORGANISM: Artificial Sequence
<220> FEATURE:
<223> OTHER INFORMATION: Pri-let-7a-1-RT-R
```

<400> SEQUENCE: 22
gattcctttt caccattcac c                                              21

<210> SEQ ID NO 23
<211> LENGTH: 21
<212> TYPE: DNA
<213> ORGANISM: Artificial Sequence
<220> FEATURE:
<223> OTHER INFORMATION: Pri-let-7a-1-RT-F

<400> SEQUENCE: 23
tttctatcag accgcctgga t                                              21

<210> SEQ ID NO 24
<211> LENGTH: 20
<212> TYPE: DNA
<213> ORGANISM: Artificial Sequence
<220> FEATURE:
<223> OTHER INFORMATION: Pri-let-7g-RT-R

<400> SEQUENCE: 24
cctgtctcaa gtgcatcctg                                                20

<210> SEQ ID NO 25
<211> LENGTH: 20
<212> TYPE: DNA
<213> ORGANISM: Artificial Sequence
<220> FEATURE:
<223> OTHER INFORMATION: Pri-let-7g-RT-F

<400> SEQUENCE: 25
cagagatgag cagggtgacg                                                20

<210> SEQ ID NO 26
<211> LENGTH: 21
<212> TYPE: DNA
<213> ORGANISM: Artificial Sequence
<220> FEATURE:
<223> OTHER INFORMATION: Pri-miR-16-1-RT-R

<400> SEQUENCE: 26
aggtgcaggc catattgtgc t                                              21

<210> SEQ ID NO 27
<211> LENGTH: 22
<212> TYPE: DNA
<213> ORGANISM: Artificial Sequence
<220> FEATURE:
<223> OTHER INFORMATION: Pri-miR-16-1-RT-F

<400> SEQUENCE: 27
ctgaaaagac tatcaataaa ac                                             22

<210> SEQ ID NO 28
<211> LENGTH: 22
<212> TYPE: DNA
<213> ORGANISM: Artificial Sequence
<220> FEATURE:
<223> OTHER INFORMATION: Mature let-7a-RT-F

<400> SEQUENCE: 28
tgaggtagta ggttgtatag tt                                             22

<210> SEQ ID NO 29
<211> LENGTH: 22

```
<212> TYPE: DNA
<213> ORGANISM: Artificial Sequence
<220> FEATURE:
<223> OTHER INFORMATION: Mature let-7b-RT-F

<400> SEQUENCE: 29
tgaggtagta ggttgtgtgg tt                                              22

<210> SEQ ID NO 30
<211> LENGTH: 22
<212> TYPE: DNA
<213> ORGANISM: Artificial Sequence
<220> FEATURE:
<223> OTHER INFORMATION: Mature let-7c-RT-F

<400> SEQUENCE: 30
tgaggtagta ggttgtatgg tt                                              22

<210> SEQ ID NO 31
<211> LENGTH: 22
<212> TYPE: DNA
<213> ORGANISM: Artificial Sequence
<220> FEATURE:
<223> OTHER INFORMATION: Mature let-7d-RT-F

<400> SEQUENCE: 31
agaggtagta ggttgcatag tt                                              22

<210> SEQ ID NO 32
<211> LENGTH: 22
<212> TYPE: DNA
<213> ORGANISM: Artificial Sequence
<220> FEATURE:
<223> OTHER INFORMATION: Mature let-7e-RT-F

<400> SEQUENCE: 32
tgaggtagga ggttgtatag tt                                              22

<210> SEQ ID NO 33
<211> LENGTH: 22
<212> TYPE: DNA
<213> ORGANISM: Artificial Sequence
<220> FEATURE:
<223> OTHER INFORMATION: Mature let-7f-RT-F

<400> SEQUENCE: 33
tgaggtagta gattgtatag tt                                              22

<210> SEQ ID NO 34
<211> LENGTH: 22
<212> TYPE: DNA
<213> ORGANISM: Artificial Sequence
<220> FEATURE:
<223> OTHER INFORMATION: Mature let-7g-RT-F

<400> SEQUENCE: 34
tgaggtagta gtttgtacag tt                                              22

<210> SEQ ID NO 35
<211> LENGTH: 22
<212> TYPE: DNA
<213> ORGANISM: Artificial Sequence
<220> FEATURE:
<223> OTHER INFORMATION: Mature let-7i-RT-F

<400> SEQUENCE: 35
```
tgaggtagta gtttgtgctg tt                                      22

<210> SEQ ID NO 36
<211> LENGTH: 22
<212> TYPE: DNA
<213> ORGANISM: Artificial Sequence
<220> FEATURE:
<223> OTHER INFORMATION: Mature miR-98-RT-F

<400> SEQUENCE: 36
tgaggtagta agttgtattg tt                                      22

<210> SEQ ID NO 37
<211> LENGTH: 22
<212> TYPE: DNA
<213> ORGANISM: Artificial Sequence
<220> FEATURE:
<223> OTHER INFORMATION: Mature miR-16-RT-F

<400> SEQUENCE: 37
tagcagcacg taaatattgg cg                                      22

<210> SEQ ID NO 38
<211> LENGTH: 21
<212> TYPE: DNA
<213> ORGANISM: Artificial Sequence
<220> FEATURE:
<223> OTHER INFORMATION: Mature miR-21-RT-F

<400> SEQUENCE: 38
caacaccagt cgatgggctg t                                       21

<210> SEQ ID NO 39
<211> LENGTH: 20
<212> TYPE: DNA
<213> ORGANISM: Artificial Sequence
<220> FEATURE:
<223> OTHER INFORMATION: WINT3-RT-F

<400> SEQUENCE: 39
ggccatgaac aagcacaaca                                         20

<210> SEQ ID NO 40
<211> LENGTH: 19
<212> TYPE: DNA
<213> ORGANISM: Artificial Sequence
<220> FEATURE:
<223> OTHER INFORMATION: WINT3-RT-R

<400> SEQUENCE: 40
tgccgtggga ggtgacatt                                          19

<210> SEQ ID NO 41
<211> LENGTH: 20
<212> TYPE: DNA
<213> ORGANISM: Artificial Sequence
<220> FEATURE:
<223> OTHER INFORMATION: T (Brachyury)-RT-F

<400> SEQUENCE: 41
gcgggaaaga gcctgcagta                                         20

<210> SEQ ID NO 42
<211> LENGTH: 20
<212> TYPE: DNA
<213> ORGANISM: Artificial Sequence

```
<220> FEATURE:
<223> OTHER INFORMATION: T (Brachyury)-RT-R

<400> SEQUENCE: 42
ttccccgttc acgtacttcc                                              20

<210> SEQ ID NO 43
<211> LENGTH: 20
<212> TYPE: DNA
<213> ORGANISM: Artificial Sequence
<220> FEATURE:
<223> OTHER INFORMATION: GATA4-RT-F

<400> SEQUENCE: 43
tccaaaccag aaaacggaag                                              20

<210> SEQ ID NO 44
<211> LENGTH: 20
<212> TYPE: DNA
<213> ORGANISM: Artificial Sequence
<220> FEATURE:
<223> OTHER INFORMATION: GATA4-RT-R

<400> SEQUENCE: 44
ctgtgcccgt agtgagatga                                              20

<210> SEQ ID NO 45
<211> LENGTH: 22
<212> TYPE: DNA
<213> ORGANISM: Artificial Sequence
<220> FEATURE:
<223> OTHER INFORMATION: FOXA2-RT-F

<400> SEQUENCE: 45
ctgagcgaga tctaccagtg ga                                           22

<210> SEQ ID NO 46
<211> LENGTH: 21
<212> TYPE: DNA
<213> ORGANISM: Artificial Sequence
<220> FEATURE:
<223> OTHER INFORMATION: FOXA2-RT-R

<400> SEQUENCE: 46
agtcgttgaa ggagagcgag t                                            21

<210> SEQ ID NO 47
<211> LENGTH: 20
<212> TYPE: DNA
<213> ORGANISM: Artificial Sequence
<220> FEATURE:
<223> OTHER INFORMATION: PAX6-RT-F

<400> SEQUENCE: 47
gtgtccaacg gatgtgtgag                                              20

<210> SEQ ID NO 48
<211> LENGTH: 20
<212> TYPE: DNA
<213> ORGANISM: Artificial Sequence
<220> FEATURE:
<223> OTHER INFORMATION: PAX6-RT-R

<400> SEQUENCE: 48
ctagccaggt tgcgaagaac                                              20
```

<210> SEQ ID NO 49
<211> LENGTH: 20
<212> TYPE: DNA
<213> ORGANISM: Artificial Sequence
<220> FEATURE:
<223> OTHER INFORMATION: NES (Nestin)-RT-F

<400> SEQUENCE: 49
aagaaataaa tcaggggggca                                            20

<210> SEQ ID NO 50
<211> LENGTH: 20
<212> TYPE: DNA
<213> ORGANISM: Artificial Sequence
<220> FEATURE:
<223> OTHER INFORMATION: NES (Nestin)-RT-R

<400> SEQUENCE: 50
caggttctct tcctcttcca                                             20

<210> SEQ ID NO 51
<211> LENGTH: 630
<212> TYPE: DNA
<213> ORGANISM: Artificial Sequence
<220> FEATURE:
<223> OTHER INFORMATION: LIN28A

<400> SEQUENCE: 51
atgggctccg tgtccaacca gcagtttgca ggtggctgcg ccaaggcggc agaagaggcg      60
cccgaggagg cgccggagga cgcggcccgg gcggcggacg agcctcagct gctgcacggt     120
gcgggcatct gtaagtggtt caacgtgcgc atggggttcg gcttcctgtc catgaccgcc     180
cgcgccgggg tcgcgctcga ccccccagtg gatgtctttg tgcaccagag taagctgcac     240
atggaagggt tccggagctt gaaggagggt gaggcagtgg agttcacctt taagaagtca     300
gccaagggtc tggaatccat ccgtgtcacc ggacctggtg gagtattctg tattgggagt     360
gagaggcggc caaaaggaaa gagcatgcag aagcgcagat caaaaggaga caggtgctac     420
aactgtggag gtctagatca tcatgccaag gaatgcaagc tgccacccca gcccaagaag     480
tgccacttct gccagagcat cagccatatg gtagcctcat gtccgctgaa ggcccagcag     540
ggccctagtg cacagggaaa gccaacctac tttcgagagg aagaagaaga atccacagc     600 cctaccctgc tcccggaggc acagaattga                                      630

<210> SEQ ID NO 52
<211> LENGTH: 209
<212> TYPE: PRT
<213> ORGANISM: Artificial Sequence
<220> FEATURE:
<223> OTHER INFORMATION: LIN28A

<400> SEQUENCE: 52

Met Gly Ser Val Ser Asn Gln Gln Phe Ala Gly Gly Cys Ala Lys Ala
1               5                  10                  15

Ala Glu Glu Ala Pro Glu Glu Ala Pro Glu Asp Ala Ala Arg Ala Ala
            20                  25                  30

Asp Glu Pro Gln Leu Leu His Gly Ala Gly Ile Cys Lys Trp Phe Asn
        35                  40                  45

Val Arg Met Gly Phe Gly Phe Leu Ser Met Thr Ala Arg Ala Gly Val
    50                  55                  60

Ala Leu Asp Pro Pro Val Asp Val Phe Val His Gln Ser Lys Leu His

```
                 65                   70                  75                  80
Met Glu Gly Phe Arg Ser Leu Lys Glu Gly Glu Ala Val Glu Phe Thr
                            85                  90                  95

Phe Lys Lys Ser Ala Lys Gly Leu Glu Ser Ile Arg Val Thr Gly Pro
                100                 105                 110

Gly Gly Val Phe Cys Ile Gly Ser Glu Arg Arg Pro Lys Gly Lys Ser
                115                 120                 125

Met Gln Lys Arg Arg Ser Lys Gly Asp Arg Cys Tyr Asn Cys Gly Gly
            130                 135                 140

Leu Asp His His Ala Lys Glu Cys Lys Leu Pro Pro Gln Pro Lys Lys
145                 150                 155                 160

Cys His Phe Cys Gln Ser Ile Ser His Met Val Ala Ser Cys Pro Leu
                165                 170                 175

Lys Ala Gln Gln Gly Pro Ser Ala Gln Gly Lys Pro Thr Tyr Phe Arg
                180                 185                 190

Glu Glu Glu Glu Glu Ile His Ser Pro Thr Leu Leu Pro Glu Ala Gln
            195                 200                 205

Asn

<210> SEQ ID NO 53
<211> LENGTH: 1101
<212> TYPE: DNA
<213> ORGANISM: Artificial Sequence
<220> FEATURE:
<223> OTHER INFORMATION: SET7/9

<400> SEQUENCE: 53
atggatagcg acgacgagat ggtggaggag gcggtggaag ggcacctgga cgatgacgga      60
ttaccgcacg ggttctgcac agtcacctac tcctccacag acagatttga ggggaacttt     120
gttcacggag aaaagaacgg acggggaag ttcttcttct ttgatggcag caccctggag      180
gggtattatg tggatgatgc cttgcagggc caggagtttt acacttacga agatggggga     240
gttctccagg gcacgtatgt agacggagag ctgaacggtc cagcccagga aatatgacaca    300 gatgggagac tgatcttcaa ggggcagtat aaagataaca ttcgtcatgg agtgtgctgg     360
atatattacc cagatggagg aagccttgta ggagaagtaa atgaagatgg ggagatgact     420
ggagagaaga tagcctatgt gtaccctgat gagaggaccg cactttatgg gaaatttatt     480
gatggagaga tgatagaagg caaactggct acccttatgt ccactgaaga agggaggcct     540
cactttgaac tgatgcctgg aaattcagtg taccactttg ataagtcgac ttcatcttgc     600
atttctacca atgctcttct tccagatcct tatgaatcag aaagggttta tgttgctgaa     660
tctcttattt ccagtgctgg agaaggactt ttttcaaagg tagctgtggg acctaatact     720
gttatgtctt tttataatgg agttcgaatt acacaccaag aggttgacag cagggactgg     780
gcccttaatg ggaacacccct ctcccttgat gaagaaacgg tcattgatgt gcctgagccc     840
tataaccacg tatccaagta ctgtgcctcc ttgggacaca aggcaaatca ctccttcact     900
ccaaactgca tctacgatat gtttgtccac cccgttttg ggcccatcaa atgcatccgc      960
accctgagag cagtggaggc cgatgaagag ctcaccgttg cctatggcta tgaccacagc    1020
ccccccggga agagtgggcc tgaagcccct gagtggtacc aggtggagct gaaggccttc    1080
caggccaccc agcaaaagtg a                                              1101

<210> SEQ ID NO 54
<211> LENGTH: 366
```

```
<212> TYPE: PRT
<213> ORGANISM: Artificial Sequence
<220> FEATURE:
<223> OTHER INFORMATION: SET7/9

<400> SEQUENCE: 54
```

| | | | | | | | | | | | | | | |
|---|---|---|---|---|---|---|---|---|---|---|---|---|---|---|
| Met | Asp | Ser | Asp | Glu | Met | Val | Glu | Ala | Val | Glu | Gly | His | Leu | |
| 1 | | | | 5 | | | | | 10 | | | | | 15 |
| Asp | Asp | Asp | Gly | Leu | Pro | His | Gly | Phe | Cys | Thr | Val | Thr | Tyr | Ser | Ser |
| | | | 20 | | | | | 25 | | | | | 30 | |
| Thr | Asp | Arg | Phe | Glu | Gly | Asn | Phe | Val | His | Gly | Glu | Lys | Asn | Gly | Arg |
| | | | 35 | | | | | 40 | | | | | 45 | |
| Gly | Lys | Phe | Phe | Phe | Phe | Asp | Gly | Ser | Thr | Leu | Glu | Gly | Tyr | Tyr | Val |
| | 50 | | | | | 55 | | | | | 60 | | | | |
| Asp | Asp | Ala | Leu | Gln | Gly | Gln | Gly | Val | Tyr | Thr | Tyr | Glu | Asp | Gly | Gly |
| 65 | | | | | 70 | | | | | 75 | | | | | 80 |
| Val | Leu | Gln | Gly | Thr | Tyr | Val | Asp | Gly | Glu | Leu | Asn | Gly | Pro | Ala | Gln |
| | | | | 85 | | | | | 90 | | | | | 95 | |
| Glu | Tyr | Asp | Thr | Asp | Gly | Arg | Leu | Ile | Phe | Lys | Gly | Gln | Tyr | Lys | Asp |
| | | | 100 | | | | | 105 | | | | | 110 | | |
| Asn | Ile | Arg | His | Gly | Val | Cys | Trp | Ile | Tyr | Tyr | Pro | Asp | Gly | Gly | Ser |
| | | 115 | | | | | 120 | | | | | 125 | | | |
| Leu | Val | Gly | Glu | Val | Asn | Glu | Asp | Gly | Glu | Met | Thr | Gly | Glu | Lys | Ile |
| | 130 | | | | | 135 | | | | | 140 | | | | |
| Ala | Tyr | Val | Tyr | Pro | Asp | Glu | Arg | Thr | Ala | Leu | Tyr | Gly | Lys | Phe | Ile |
| 145 | | | | | 150 | | | | | 155 | | | | | 160 |
| Asp | Gly | Glu | Met | Ile | Glu | Gly | Lys | Leu | Ala | Thr | Leu | Met | Ser | Thr | Glu |
| | | | | 165 | | | | | 170 | | | | | 175 | |
| Glu | Gly | Arg | Pro | His | Phe | Glu | Leu | Met | Pro | Gly | Asn | Ser | Val | Tyr | His |
| | | | 180 | | | | | 185 | | | | | 190 | | |
| Phe | Asp | Lys | Ser | Thr | Ser | Ser | Cys | Ile | Ser | Thr | Asn | Ala | Leu | Leu | Pro |
| | | 195 | | | | | 200 | | | | | 205 | | | |
| Asp | Pro | Tyr | Glu | Ser | Glu | Arg | Val | Tyr | Val | Ala | Glu | Ser | Leu | Ile | Ser |
| | 210 | | | | | 215 | | | | | 220 | | | | |
| Ser | Ala | Gly | Glu | Gly | Leu | Phe | Ser | Lys | Val | Ala | Val | Gly | Pro | Asn | Thr |
| 225 | | | | | 230 | | | | | 235 | | | | | 240 |
| Val | Met | Ser | Phe | Tyr | Asn | Gly | Val | Arg | Ile | Thr | His | Gln | Glu | Val | Asp |
| | | | | 245 | | | | | 250 | | | | | 255 | |
| Ser | Arg | Asp | Trp | Ala | Leu | Asn | Gly | Asn | Thr | Leu | Ser | Leu | Asp | Glu | Glu |
| | | | 260 | | | | | 265 | | | | | 270 | | |
| Thr | Val | Ile | Asp | Val | Pro | Glu | Pro | Tyr | Asn | His | Val | Ser | Lys | Tyr | Cys |
| | | 275 | | | | | 280 | | | | | 285 | | | |
| Ala | Ser | Leu | Gly | His | Lys | Ala | Asn | His | Ser | Phe | Thr | Pro | Asn | Cys | Ile |
| | 290 | | | | | 295 | | | | | 300 | | | | |
| Tyr | Asp | Met | Phe | Val | His | Pro | Arg | Phe | Gly | Pro | Ile | Lys | Cys | Ile | Arg |
| 305 | | | | | 310 | | | | | 315 | | | | | 320 |
| Thr | Leu | Arg | Ala | Val | Glu | Ala | Asp | Glu | Glu | Leu | Thr | Val | Ala | Tyr | Gly |
| | | | | 325 | | | | | 330 | | | | | 335 | |
| Tyr | Asp | His | Ser | Pro | Pro | Gly | Lys | Ser | Gly | Pro | Glu | Ala | Pro | Glu | Trp |
| | | | 340 | | | | | 345 | | | | | 350 | | |
| Tyr | Gln | Val | Glu | Leu | Lys | Ala | Phe | Gln | Ala | Thr | Gln | Gln | Lys | | |
| | | | 355 | | | | | 360 | | | | | 365 | | |

```
<210> SEQ ID NO 55
<211> LENGTH: 11
```

```
<212> TYPE: PRT
<213> ORGANISM: Artificial Sequence
<220> FEATURE:
<223> OTHER INFORMATION: Histone H3 (1-11)

<400> SEQUENCE: 55

Ala Arg Thr Lys Gln Thr Ala Arg Lys Ser Thr
1               5                   10

<210> SEQ ID NO 56
<211> LENGTH: 15
<212> TYPE: PRT
<213> ORGANISM: Artificial Sequence
<220> FEATURE:
<223> OTHER INFORMATION: p53 (365-379)

<400> SEQUENCE: 56

His Ser Ser His Leu Lys Ser Lys Lys Gly Gln Ser Thr Ser Arg
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: TAF10 (182-196)

<400> SEQUENCE: 57

Gly Ser Ser Arg Ser Lys Ser Lys Asp Arg Lys Tyr Thr Leu Thr
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: DNMT1 (135-149)

<400> SEQUENCE: 58

Pro Arg Thr Pro Arg Arg Ser Lys Ser Asp Gly Glu Ala Lys Arg
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: ERa (295-309)

<400> SEQUENCE: 59

Pro Leu Met Ile Lys Arg Ser Lys Lys Asn Ser Leu Ala Leu Ser
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: E2F1 (178-192)

<400> SEQUENCE: 60

Gln Leu Ile Ala Lys Lys Ser Lys Asn His Ile Gln Trp Leu Gly
1               5                   10                  15

<210> SEQ ID NO 61
<211> LENGTH: 15
<212> TYPE: PRT
```

```
<213> ORGANISM: Artificial Sequence
<220> FEATURE:
<223> OTHER INFORMATION: LIN28A (128-142)

<400> SEQUENCE: 61

Ser Met Gln Lys Arg Arg Ser Lys Gly Asp Arg Cys Tyr Asn Cys
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: LIN28B (118-132)

<400> SEQUENCE: 62

Thr Leu Gln Lys Arg Lys Pro Lys Gly Asp Arg Cys Tyr Asn Cys
1               5                   10                  15
```